United States Patent
Arakawa et al.

(10) Patent No.: US 11,604,194 B2
(45) Date of Patent: Mar. 14, 2023

(54) METHOD FOR DETECTING CASTRATION-RESISTANT PROSTATE CANCER AND DETECTION REAGENT

(71) Applicants: PUBLIC UNIVERSITY CORPORATION YOKOHAMA CITY UNIVERSITY, Yokohama (JP); TOSOH CORPORATION, Shunan (JP)

(72) Inventors: Noriaki Arakawa, Yokohama (JP); Hisashi Hirano, Yokohama (JP); Hiroji Uemura, Yokohama (JP); Yusuke Ito, Yokohama (JP); Shohei Myoba, Ayase (JP); Norihisa Ohtake, Ayase (JP)

(73) Assignees: PUBLIC UNIVERSITY CORPORATION YOKOHAMA CITY UNIVERSITY, Yokohama (JP); TOSOH CORPORATION, Shunan (JP)

(*) Notice: Subject to any disclaimer, the term of this patent is extended or adjusted under 35 U.S.C. 154(b) by 1185 days.

(21) Appl. No.: 16/080,577

(22) PCT Filed: Feb. 23, 2017

(86) PCT No.: PCT/JP2017/006705
§ 371 (c)(1),
(2) Date: Aug. 28, 2018

(87) PCT Pub. No.: WO2017/150314
PCT Pub. Date: Sep. 8, 2017

(65) Prior Publication Data
US 2021/0190786 A1    Jun. 24, 2021

(30) Foreign Application Priority Data

Feb. 29, 2016  (JP) .............................. JP2016-037135

(51) Int. Cl.
| | | |
|---|---|---|
| *G01N 33/574* | (2006.01) | |
| *G01N 33/68* | (2006.01) | |
| *C07K 14/475* | (2006.01) | |
| *C07K 14/525* | (2006.01) | |
| *C07K 16/22* | (2006.01) | |

(52) U.S. Cl.
CPC ..... *G01N 33/57434* (2013.01); *C07K 14/475* (2013.01); *C07K 14/525* (2013.01); *C07K 16/22* (2013.01); *G01N 33/6863* (2013.01); *G01N 33/6893* (2013.01)

(58) Field of Classification Search
CPC ........... G01N 33/6893; G01N 33/6863; G01N 33/574; G01N 33/57434; C07K 14/475; C07K 14/525
See application file for complete search history.

(56) References Cited

U.S. PATENT DOCUMENTS

| | | |
|---|---|---|
| 2004/0053325 A1 | 3/2004 | Breit et al. |
| 2009/0004181 A1 | 1/2009 | Breit |
| 2010/0159608 A1 | 6/2010 | Hess et al. |
| 2010/0261284 A1 | 10/2010 | Spanuth |
| 2011/0033886 A1 | 2/2011 | Hess et al. |
| 2011/0039284 A1 | 2/2011 | Breit et al. |
| 2011/0065204 A1 | 3/2011 | Wollert et al. |
| 2011/0263443 A1 | 10/2011 | Hess et al. |
| 2015/0239968 A1* | 8/2015 | Wischhusen ........... A61K 45/06 435/320.1 |
| 2017/0010280 A1 | 1/2017 | Tanaka et al. |

FOREIGN PATENT DOCUMENTS

| | | |
|---|---|---|
| JP | 2003-532079 A | 10/2009 |
| JP | 2009-545735 A | 12/2009 |
| JP | 2010-528275 A | 8/2010 |
| JP | 2011-501136 A | 1/2011 |
| JP | 2011-509403 A | 3/2011 |
| JP | 2011-523051 A | 8/2011 |
| JP | 2011-190262 A | 9/2011 |
| JP | 2012-515335 A | 7/2012 |
| JP | 2013-174614 A | 9/2013 |
| WO | 2011/102461 A1 | 8/2011 |
| WO | 2012/138919 A2 | 10/2012 |
| WO | 2015/108077 A1 | 7/2015 |

OTHER PUBLICATIONS

Anti-GDF15 antibody product datasheet from Sigma-Aldrich. "HPA011191"; www.sigmaaldrich.com/US/en/product/sigma/hpa011191; downloaded May 18, 2022.*
Corre et al. Concise review: Growth differentiation factor 15 in pathology: a clinical role? Stem Cells Translat Med 2: 946-952, 2013.*
Costa et al. Three epigenetic biomarkers, GDF15, TMEFF2, and VIM, accurately predict bladder cancer from DNA-based analyses of urine samples. Clin Cancer Res 16(23): 5842-5851, 2010.*
Li et al. Prognostic and predictive biomarkers for men with castration-resistant prostate cancer. In: Preedy V., Patel V. (eds) Biomarkers in Cancer. Springer, Dordrecht, https://doi.org/10.1007/978-94-007-7744-6_13-1, 2014.*
Maetzler et al. GDF15/MIC1 and MMP9 cerebrospinal fluid levels in Parkinson's dsease and lewy body dementia. PLoS One 11(3): e0149349, 2016.*
Mahon et al. Cytokine profiling of docetaxel-resistant castration-resistant prostate cancer. Brit J Cancer 112: 1340-1348, 2015.*

(Continued)

*Primary Examiner* — Bridget E Bunner
(74) *Attorney, Agent, or Firm* — Sughrue Mion, PLLC

(57) ABSTRACT

The present invention aims to provide a method for simply and highly accurately detecting castration-resistant prostate cancer (CRPC), and a reagent that can be used for this method. By measuring the level of GDF15 propeptide present in a sample as a novel detection marker for CRPC, acquisition of castration resistance in a prostate cancer patient during or after endocrine therapy is detected. An antibody that specifically recognizes GDF15 propeptide is included in the CRPC detection reagent.

11 Claims, 17 Drawing Sheets
Specification includes a Sequence Listing.

(56) References Cited

OTHER PUBLICATIONS

Mimeault et al. Marked improvement of cytotoxic effects induced by docetaxel on highly metastatic and androgen-independent prostate cancer cells by downregulating macrophage inhibitory cytokine-1. Brit J Cancer 108: 1079-1091, 2013.*
Uemura et al. Novel biomarker of specific castration-resistant prostate cancer (CRPC) by exploring the proteome analysis. J Clin Oncol 35(6) Supplement: p. 247, Feb. 20, 2017.*
Urakawa et al. GDF15 derived from both tumor-associated macrophages and esopahgeal squamous cell carcinomas contributes to tumor progression via Akt and Erk pathways. Lab Invest 95: 491-503, 2015.*
Asne R. Bauskin et al., "The Propeptide Mediates Formation of Stromal Stores of PROMIC-1: Role in Determining Prostate Cancer Outcome," Cancer Research, Mar. 15, 2005, pp. 2330-2336, vol. 65, No. 6.
L. Magadoux et al., "Emerging targets to monitor and overcome docetaxel resistance in castration resistant prostate cancer (Review)," International Journal of Oncology, 2014, pp. 919-928, vol. 45.
P. Vanhara et al., "Growth/differentiation factor-15: prostate cancer suppressor or promoter?" Prostate Cancer and Prostatic Diseases, Feb. 28, 2012, pp. 320-328, vol. 15, No. 4.
Xingya Wang et al., "The diverse roles of nonsteroidal anti-inflammatory drug activated gene (NAG-1/GDF15) in cancer," Biochemical Pharmacology, 2013, pp. 597-606, vol. 85.
David A. Brown et al., "Macrophage Inhibitory Cytokine 1: A New Prognostic Marker in Prostate Cancer," Clinical Cancer Research, Nov. 1, 2009, pp. 6658-6664 (8 pages), vol. 15, No. 21.
Anne Cathrine Staff et al., "Elevated Plasma Growth Differentiation Factor-15 Correlates with Lymph Node Metastases and Poor Survival in Endometrial Cancer," Clinical Cancer Research, Jul. 15, 2011, pp. 4825-4833 (10 pages), vol. 17, No. 14.
David A. Brown et al., "MIC-1 Serum Level and Genotype: Associations with Progress and Prognosis of Colorectal Carcinoma," Clinical Cancer Research, Jul. 2003, pp. 2642-2650 (10 pages), vol. 9.
Jens Koopmann et al., "Serum Markers in Patients with Resectable Pancreatic Adenocarcinoma: Macrophage Inhibitory Cytokine 1 versus CA19-9," Clinical Cancer Research, Jan. 15, 2006, pp. 442-446 (6 pages), vol. 12, No. 2.
David A. Brown et al., "Measurement of Serum Levels of Macrophage Inhibitory Cytokine 1 Combined with Prostate-Specific Antigen Improves Prostate Cancer Diagnosis," Clinical Cancer Research, Jan. 1, 2006, pp. 89-96 (9 pages), vol. 12, No. 1.
Katri S. Selander et al., "Serum Macrophage Inhibitory Cytokine-1 Concentrations Correlate with the Presence of Prostate Cancer Bone Metastases," Cancer Epidemiology, Biomarkers & Prevention, Mar. 2007, pp. 532-537 (7 pages), vol. 16, No. 3.
Fredrik E. Wiklund et al., "Macrophage inhibitory cytokine-1 (MIC-1/GDF15): a new marker of all-cause mortality," Aging Cell, 2010, pp. 1057-1064, vol. 9.
International Search Report of PCT/JP2017/006705 dated May 16, 2017.
International Preliminary Report on Patentability of PCT/JP2017/006705 dated Sep. 13, 2018.
Communication dated Jan. 9, 2020, from the European Patent Office in European Application No. 17759780.4.
Martin Boegemann et al., "Present, Emerging and Possible Future Biomarkers in Castration Resistant Prostate Cancer (CRPC)", Current Cancer Drug Targets, May 5, 2015, vol. 15, No. 3, pp. 243-255 (13 pages total).
Dev Karan et al., "Dysregulated expression of MIC-1/PDF in human prostate tumor cells", Biochemical and Biophysical Research Communications, Apr. 11, 2003, vol. 305, pp. 598-604 (7 pages total).
Fairlie et al., "MIC-1 is a novel TGF-β superfamily cytokine associated with macrophage activation", Journal of Leukocyte Biology, vol. 65, No. 1, pp. 2-5, Jan. 1999 (4 pages total).
Office Action dated May 31, 2022 issued from European Patent Office in EP Application No. 17759780.4.

* cited by examiner

Signal peptide ↔ Propeptide

1   MPGQELRTVN GSQMLLVLLV LSWLPHGGAL SLAEASRASF PGPSELHSED
                                   |30
51  SRFRELRKRY EDLLTRLRAN QSWEDSNTDL VPAPAVRILT PEVRLGSGGH

101 LHLRISRAAL PEGLPEASRL HRALFRLSPT ASRSWDVTRP LRRQLSLARP

Propeptide ↔ Mature

151 QAPALHLRLS PPPSQSDQLL AESSSARPQL ELHLRPQAAR GRRRARARNG
                                                     |195
201 DHCPLGPGRC CRLHTVRASL EDLGNADNVL SPREVQVTMC IGACPSQFRA

251 ANMHAQIKTS LHRLKPDTVP APCCVPASYN PMVLIQKTDT GVSLQTYDDL

301 LAKDCHCI (SEQ ID NO.: 2)

Fig. 1

SEQUENCE LISTING

```
<160> NUMBER OF SEQ ID NOS: 8

<210> SEQ ID NO 1
<211> LENGTH: 1220
<212> TYPE: DNA
<213> ORGANISM: Homo sapiens
<220> FEATURE:
<221> NAME/KEY: CDS
<222> LOCATION: (33)..(956)

<400> SEQUENCE: 1
agtcccagct cagagccgca acctgcacag cc atg ccc ggg caa gaa ctc agg      53
                                    Met Pro Gly Gln Glu Leu Arg
                                    1               5 acg gtg aat ggc tct cag atg ctc ctg gtg ttg ctg gtg ctc tcg tgg    101
Thr Val Asn Gly Ser Gln Met Leu Leu Val Leu Leu Val Leu Ser Trp
        10                  15                  20
```

```
ctg ccg cat ggg ggc gcc ctg tct ctg gcc gag gcg agc cgc gca agt      149
Leu Pro His Gly Gly Ala Leu Ser Leu Ala Glu Ala Ser Arg Ala Ser
    25                  30                  35 ttc ccg gga ccc tca gag ttg cac tcc gaa gac tcc aga ttc cga gag      197
Phe Pro Gly Pro Ser Glu Leu His Ser Glu Asp Ser Arg Phe Arg Glu
40                  45                  50                  55 ttg cgg aaa cgc tac gag gac ctg cta acc agg ctg cgg gcc aac cag      245
Leu Arg Lys Arg Tyr Glu Asp Leu Leu Thr Arg Leu Arg Ala Asn Gln
                    60                  65                  70 agc tgg gaa gat tcg aac acc gac ctc gtc ccg gcc cct gca gtc cgg      293
Ser Trp Glu Asp Ser Asn Thr Asp Leu Val Pro Ala Pro Ala Val Arg
                75                  80                  85 ata ctc acg cca gaa gtg cgg ctg gga tcc ggc ggc cac ctg cac ctg      341
Ile Leu Thr Pro Glu Val Arg Leu Gly Ser Gly Gly His Leu His Leu
            90                  95                  100 cgt atc tct cgg gcc gcc ctt ccc gag ggg ctc ccc gag gcc tcc cgc      389
Arg Ile Ser Arg Ala Ala Leu Pro Glu Gly Leu Pro Glu Ala Ser Arg
        105                 110                 115 ctt cac cgg gct ctg ttc cgg ctg tcc ccg acg gcg tca agg tcg tgg      437
Leu His Arg Ala Leu Phe Arg Leu Ser Pro Thr Ala Ser Arg Ser Trp
120                 125                 130                 135 gac gtg aca cga ccg ctg cgg cgt cag ctc agc ctt gca aga ccc cag      485
Asp Val Thr Arg Pro Leu Arg Arg Gln Leu Ser Leu Ala Arg Pro Gln
                    140                 145                 150 gcg ccc gcg ctg cac ctg cga ctg tcg ccg ccg tcg cag tcg gac          533
Ala Pro Ala Leu His Leu Arg Leu Ser Pro Pro Ser Gln Ser Asp
                155                 160                 165 caa ctg ctg gca gaa tct tcg tcc gca cgg ccc cag ctg gag ttg cac      581
Gln Leu Leu Ala Glu Ser Ser Ser Ala Arg Pro Gln Leu Glu Leu His
            170                 175                 180 ttg cgg ccg caa gcc gcc agg ggg cgc cgc aga gcg cgt gcg cgc aac      629
Leu Arg Pro Gln Ala Ala Arg Gly Arg Arg Arg Ala Arg Ala Arg Asn
185                 190                 195 ggg gac cac tgt ccg ctc ggg ccc ggg cgt tgc tgc cgt ctg cac acg      677
Gly Asp His Cys Pro Leu Gly Pro Gly Arg Cys Cys Arg Leu His Thr
200                 205                 210                 215 gtc cgc gcg tcg ctg gaa gac ctg ggc tgg gcc gat tgg gtg ctg tcg      725
Val Arg Ala Ser Leu Glu Asp Leu Gly Trp Ala Asp Trp Val Leu Ser
                    220                 225                 230 cca cgg gag gtg caa gtg acc atg tgc atc ggc gcg tgc ccg agc cag      773
Pro Arg Glu Val Gln Val Thr Met Cys Ile Gly Ala Cys Pro Ser Gln
                235                 240                 245 ttc cgg gcg gca aac atg cac gcg cag atc aag acg agc ctg cac cgc      821
Phe Arg Ala Ala Asn Met His Ala Gln Ile Lys Thr Ser Leu His Arg
            250                 255                 260 ctg aag ccc gac acg gtg cca gcg ccc tgc tgc gtg ccc gcc agc tac      869
Leu Lys Pro Asp Thr Val Pro Ala Pro Cys Cys Val Pro Ala Ser Tyr
265                 270                 275 aat ccc atg gtg ctc att caa aag acc gac acc ggg gtg tcg ctc cag      917
Asn Pro Met Val Leu Ile Gln Lys Thr Asp Thr Gly Val Ser Leu Gln
280                 285                 290                 295 acc tat gat gac ttg tta gcc aaa gac tgc cac tgc ata tgagcagtcc      966
Thr Tyr Asp Asp Leu Leu Ala Lys Asp Cys His Cys Ile
                    300                 305 tggtccttcc actgtgcacc tgcgcggagg acgcgacctc agttgtcctg ccctgtggaa    1026
tgggctcaag gttcctgaga cacccgattc ctgcccaaac agctgtattt ataaagtct     1086 gttatttatt attaatttat tggggtgacc ttcttgggga ctcgggggct ggtctgatgg    1146
```

```
aactgtgtat ttatttaaaa ctctggtgat aaaaataaag ctgtctgaac tgttaaaaaa      1206
aaaaaaaaaa aaaa                                                        1220
```

<210> SEQ ID NO 2
<211> LENGTH: 308
<212> TYPE: PRT
<213> ORGANISM: Homo sapiens

<400> SEQUENCE: 2

```
Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305
```

<210> SEQ ID NO 3
<211> LENGTH: 31
<212> TYPE: DNA
<213> ORGANISM: Artificial Sequence
<220> FEATURE:
<223> OTHER INFORMATION: Secreted iGDPP forward primer -continued

<400> SEQUENCE: 3
cgatgacgac aagcttctgt ctctggccga g  31

<210> SEQ ID NO 4
<211> LENGTH: 33
<212> TYPE: DNA
<213> ORGANISM: Artificial Sequence
<220> FEATURE:
<223> OTHER INFORMATION: Secreted iGDPP reverse primer

<400> SEQUENCE: 4
cagaactttg cagatatcgg cggcttgcgg ccg  33

<210> SEQ ID NO 5
<211> LENGTH: 33
<212> TYPE: DNA
<213> ORGANISM: Artificial Sequence
<220> FEATURE:
<223> OTHER INFORMATION: Secreted dNT37-GDPP forward primer

<400> SEQUENCE: 5
cgatgacgac aagcttgcaa gtttcccggg acc  33

<210> SEQ ID NO 6
<211> LENGTH: 31
<212> TYPE: DNA
<213> ORGANISM: Artificial Sequence
<220> FEATURE:
<223> OTHER INFORMATION: Secreted dNT59-GDPP forward primer

<400> SEQUENCE: 6
cgatgacgac aagcttcgct acgaggacct g  31

<210> SEQ ID NO 7
<211> LENGTH: 32
<212> TYPE: DNA
<213> ORGANISM: Artificial Sequence
<220> FEATURE:
<223> OTHER INFORMATION: Secreted dNT77-GDPP forward primer

<400> SEQUENCE: 7
cgatgacgac aagcttaaca ccgacctcgt cc  32

<210> SEQ ID NO 8
<211> LENGTH: 31
<212> TYPE: DNA
<213> ORGANISM: Artificial Sequence
<220> FEATURE:
<223> OTHER INFORMATION: Secreted dNT94-GDPP forward primer

<400> SEQUENCE: 8
cgatgacgac aagcttctgg gatccggcgg c  31

METHOD FOR DETECTING CASTRATION-RESISTANT PROSTATE CANCER AND DETECTION REAGENT

CROSS REFERENCE TO RELATED APPLICATIONS

This application is a National Stage of International Application No. PCT/JP2017/006705 filed Feb. 23, 2017, claiming priority based on Japanese Patent Application No. 2016-037135 filed Feb. 29, 2016.

TECHNICAL FIELD

The present invention relates to a propeptide of Growth and Differentiation Factor 15 (which is hereinafter also referred to as "GDF15") protein in blood, and a degradation product thereof; and a detection method and a detection reagent for castration-resistant prostate cancer by measurement of these.

BACKGROUND ART

Growth and differentiation factor 15 (GDF15) is a protein which is identical to macrophage inhibitory cytokine 1 (MIC-1) and nonsteroidal anti-inflammatory drug-activated gene 1 (NAG-1), and belongs to the TGF-β family. GDF15 is expressed as prepro-GDF15, which contains a signal peptide and a propeptide, and then the signal peptide is cleaved to form pro-GDF15, which is then secreted to the outside of the cell. Pro-GDF15 is stored in the extracellular matrix through the propeptide, and GDF15 forming a dimer is cleaved off from the propeptide by a furin-like protease to be released into blood (Non-patent Document 1). Full-length pro-GDF15 is reported to be separated into a fraction having a molecular weight of about 40,000, and the mature body of GDF15 is reported to be separated into a fraction having a molecular weight of about 15,000 (Non-patent Document 2).

The level of the mature body of GDF15 in blood increases in various diseases such as prostate cancer (PCa) and ovarian cancer, and also heart diseases (Patent Documents 1 to 6, Non-patent Documents 3 to 7). Further, there are discoveries on practical application of GDF15 to appetite regulation and prenatal testing (Patent Documents 7 and 8). In particular, in relation to prostatic diseases, it is known that prostate cancer causes an increase in the level of the mature body of GDF15 in blood relative to cases of benign prostatic hypertrophy (BPH), that the diagnostic performance can be increased by combination with a measured value of PSA, and that GDF15 is useful for prognostic prediction since there is a correlation between bone metastasis and the level of the mature body of GDF15 in blood (Patent Documents 9 and 10, Non-patent Documents 8 to 10).

However, all of these discoveries are on the mature body of GDF15, and GDF15 propeptide has been thought to be localized in the extracellular matrix (Non-patent Document 2). Although data of a comprehensive proteome analysis (PeptideAtlas; Protein Name: ENSP000252809, Build: Human Plasma Non-Glyco 2015-09) suggests the presence of GDF15 propeptide in blood, the presence of a degradation product of GDF15 propeptide has not been known to date. Further, detection of a disease by measurement of this protein, and its effectiveness, have not been known.

At present, the annual incidence of prostate cancer is about 60,000, and its annual mortality is about 11,000 in Japan. These numbers are now rapidly increasing. In cases of early-stage prostate cancer or locally-advanced prostate cancer, surgical therapy or radiation therapy is used, and the prognosis is good. On the other hand, in cases of metastatic advanced cancer, hormone therapy using an antiandrogen drug is carried out, and the therapy is said to be effective in about 80% of such cases. However, some cases of prostate cancer lead to development of castration-resistant prostate cancer (CRPC), wherein disease progression occurs in spite of the fact that the androgen level is suppressed to a castration level.

Conventionally, anticancer drug treatment has been carried out for CRPC patients. Recently, however, three novel therapeutic agents for CRPC (two kinds of hormone therapeutic agents and one kind of anticancer drug) have become covered by insurance in Japan, and the order of use of therapeutic agents and judgment of the timing to start anticancer drug treatment have become important.

As a method for detecting prostate cancer using a blood component such as whole blood, blood cells, serum, or plasma, a method in which a prostate-specific antigen (PSA) is detected is generally known. PSA is a serine protease purified from human seminal plasma by Wang et al. in 1979, and detection of PSA at not less than 20 ng/ml in a blood component indicates prostate cancer with a high positive rate. Therefore, the method is widely used as a test effective for, for example, screening of prostate cancer, evaluation of a therapeutic effect on prostate cancer, and follow-up after treatment.

However, the blood PSA level and the disease state of CRPC are not necessarily associated with each other, and acquisition of castration resistance cannot be easily judged based on measurement of PSA alone. Thus, at present, comprehensive follow-up including other test methods is carried out. It is said that, in patients showing high Gleason scores and patients with advanced disease stages, acquisition of castration resistance occurs in a relatively early phase. However, since definitive diagnosis based on PSA is impossible, and the period of time before acquisition of castration resistance widely varies from several months to 10 years among patients, judgment of castration resistance often becomes possible only after exacerbation of the disease state such as bone metastasis. Thus, a simpler and more accurate method for detection of acquisition of castration resistance based on blood test has been strongly demanded.

PRIOR ART DOCUMENTS

Patent Documents

[Patent Document 1] JPWO 2011-102461 A1
[Patent Document 2] JP 2009-545735 A
[Patent Document 3] JP 2010-528275 A
[Patent Document 4] JP 2011-523051 A
[Patent Document 5] JP 2012-515335 A
[Patent Document 6] JPWO 2015-108077 A1
[Patent Document 7] JP 2011-190262 A
[Patent Document 8] JP 2003-532079 A
[Patent Document 9] JP 2013-174614 A
[Patent Document 10] JP 2011-509403 A Non-Patent Documents

[Non-patent Document 1] Prostate Cancer Prostatic Dis, 2012; 15(4): 320-328
[Non-patent Document 2] Cancer Res. 2005; 65(6): 2330-2336
[Non-patent Document 3] Biochemical Pharmacology, 2013; 85: 597-606

[Non-patent Document 4] Clin Cancer Res. 2009; 15(21): 6658-6664
[Non-patent Document 5] Clin Cancer Res. 2011; 17: 4825-4833
[Non-patent Document 6] Clin Cancer Res. 2003; 9: 2642-2650
[Non-patent Document 7] Clin Cancer Res. 2006; 12: 442-446
[Non-patent Document 8] Clin Cancer Res. 2006; 12(1): 89-96
[Non-patent Document 9] Cancer Epidemiol Biomarkers Prev, 2007: 16: 532-537
[Non-patent Document 10] Aging Cell, 2010; 9: 1057-1064

SUMMARY OF THE INVENTION

Problems to be Solved by the Invention

An object of the present invention is to provide a method for simply and highly accurately detecting castration-resistant prostate cancer (CRPC), and a reagent that can be used for this method.

Means for Solving the Problems

The present inventors intensively studied to solve the above problem. As a result, the present inventors discovered that GDF15 propeptide and its degradation product are secreted into culture supernatant of a cancer cell line, and confirmed that GDF15 propeptide and its degradation product are present also in blood of cancer patients. In particular, as a result of proteome analysis of culture supernatants of prostate cancer (PCa) and castration-resistant prostate (CRPC) cell lines, it was found that not only the mature body of GDF15, but also GDF15 propeptide and its degradation product are present in the culture supernatants.

Further, as a result of intensive study, the present inventors discovered, in an immunoassay for prostate tumor and benign prostatic hypertrophy using an antibody that recognizes GDF15 propeptide, that a remarkable increase in GDF15 propeptide in blood is found in prostate cancer samples after acquisition of castration resistance, and hence that GDF15 propeptide can be a detection marker for castration-resistant prostate cancer, thereby completing the present invention.

That is, the present invention is as follows.

[1] A method for detecting castration-resistant prostate cancer, which comprises measuring the intact GDF15 propeptide level in a sample.
[2] A method for detecting castration-resistant prostate cancer, which comprises measuring the GDF15 propeptide fragments level in a sample.
[3] A method for detecting castration-resistant prostate cancer, which comprises measuring the total of the intact GDF15 propeptide level and the GDF15 propeptide fragment level in a sample.
[4] The method according to [2] or [3], wherein the GDF15 propeptide fragment contains a GDF15 propeptide fragment(s) of the following (A) and/or (B):
  (A) a GDF15 propeptide fragment having the following properties (a) and (b):
    (a) containing an amino acid sequence from the lysine of the 58th residue to at least the aspartic acid of the 167th residue in the GDF15 amino acid sequence of SEQ ID NO:2, or a sequence having an identity of not less than 80% thereto; and
    (b) separation into a fraction with a molecular weight of about 17,000 by reducing SDS-PAGE;
  (B) a GDF15 propeptide fragment having the following properties (c) and (d):
    (c) containing an amino acid sequence from the glutamic acid of the 74th residue to at least the aspartic acid of the 167th residue in the GDF15 amino acid sequence of SEQ ID NO:2, or a sequence having an identity of not less than 80% thereto; and
    (d) separation into a fraction with a molecular weight of about 15,000 by reducing SDS-PAGE.
[5] The method according to any one of [1] to [4], wherein the measurement is carried out using antigen-antibody reaction using an antibody that recognizes GDF15 propeptide.
[6] The method according to any one of [1] to [5], wherein the measurement is carried out using mass spectrometry.
[7] A reagent for detecting castration-resistant prostate cancer, which comprises an antibody that recognizes GDF15 propeptide.
[8] A GDF15 propeptide fragment having the following properties (a) and (b):
  (a) containing an amino acid sequence from the lysine of the 58th residue to at least the aspartic acid of the 167th residue in the GDF15 amino acid sequence of SEQ ID NO:2, or a sequence having an identity of not less than 80% thereto; and
  (b) separation into a fraction with a molecular weight of about 17,000 by reducing SDS-PAGE.
[9] A GDF15 propeptide fragment having the following properties (c) and (d):
  (c) containing an amino acid sequence from the glutamic acid of the 74th residue to at least the aspartic acid of the 167th residue in the GDF15 amino acid sequence of SEQ ID NO:2, or a sequence having an identity of not less than 80% thereto; and
  (d) separation into a fraction with a molecular weight of about 15,000 by reducing SDS-PAGE.

Effect of the Invention

By the present invention, a novel peptide fragment that can be a diagnostic marker for castration-resistant prostate cancer (CRPC) is provided. Further, by the present invention, a method for simply and highly accurately detecting CRPC, and a reagent that can be used for this method are provided.

The reagent of the present invention is for detection of GDF15 propeptide, and GDF15 expression regulation is located downstream of p53. It is thus assumed that therapeutic effects of existing therapeutic agents for prostate cancer, especially taxane-based anticancer drugs, are reflected. Thus, the reagent of the present invention can also be a companion diagnostic agent for treatment of prostate cancer.

BRIEF DESCRIPTION OF THE DRAWINGS

FIG. 1 is a diagram illustrating a GDF15 peptide detected in cancer cell culture supernatant. The shaded portions correspond to the peptides detected by the proteome analysis.

MODE FOR CARRYING OUT THE INVENTION

Figure 2A:
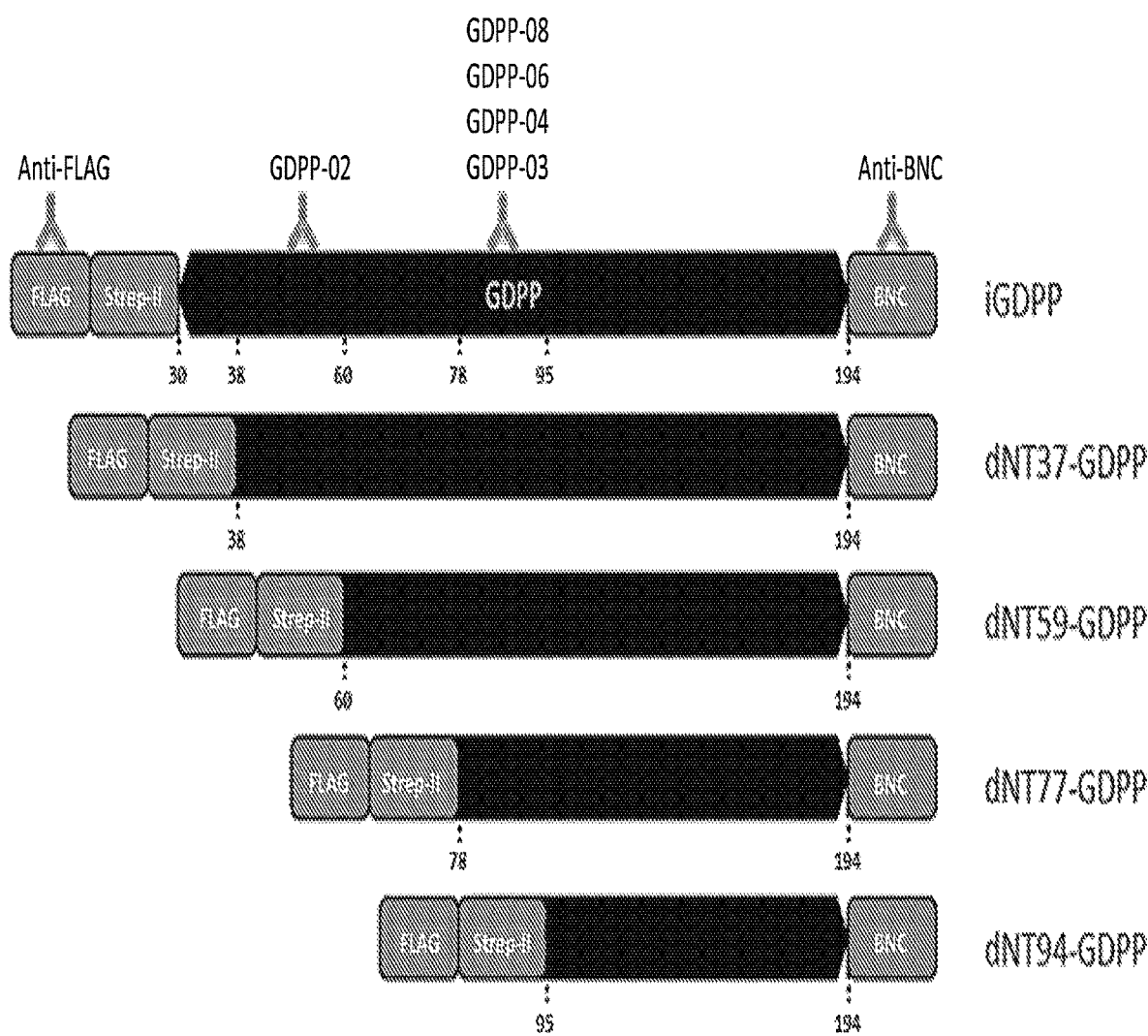
FIG. 2A is a schematic diagram illustrating the recombinant GDPPs prepared for the epitope analysis.

<1> Growth and Differentiation Factor 15 (GDF15) Propeptide Fragment of Present Invention The first mode of the present invention is a GDF15 propeptide fragment as a degradation product of GDF15 propeptide.

Based on expression and secretion modes of GDF15. GDF15 propeptide has been thought to be localized in the extracellular matrix also after secretion of the mature body of GDF15. As a result of proteome analysis of culture supernatants of PCa and CRPC cell lines by the present inventors, it was found that not only the mature body of GDF15, but also GDF15 propeptide and a degradation product thereof are present in the culture supernatants. Further, the present inventors discovered that GDF15 propeptide and its degradation product are secreted into blood. It is assumed that, as the expression level increases, secretion of GDF15 propeptide into blood occurs, and that the GDF15 propeptide undergoes a certain characteristic processing in this process, leading to the presence of the GDF15 propeptide fragment as a degradation product of the GDF15 propeptide. The presence of a degradation product (fragment) of GDF15 propeptide has not been known so far.

GDF15 propeptide (hereinafter also referred to as "GDPP") is a polypeptide of 165 residues positioned in the N-terminal side of pro-GDF15. More specifically, the GDF15 propeptide in the present description contains at least a sequence from the leucine of the 30th residue to the arginine of the 194th residue following a sequence corresponding to the signal peptide from the initiating methionine to the alanine of the 29th residue in the amino acid sequence according to cDNA of human GDF15 of SEQ ID NO:1 (GenBank Accession No.: NM_004864), or contains an amino acid sequence having an identity of not less than 80% to this sequence.

It is thought that the plurality of forms of GDF15 propeptide fragment are present, and these forms include the following two kinds of forms, which were found in the later-mentioned Examples.

One of these is a C-terminal side fragment of GDF15 propeptide formed by processing in the N-terminal side of the lysine of the 58th residue of SEQ ID NO:2 in GDPP, wherein the region from the first to 57th residues are deleted (hereinafter also referred to as "dNT57-GDPP"). More specifically, this form includes a sequence from the lysine of the 58th residue to at least the aspartic acid of the 167th residue in SEQ ID NO:2, or an amino acid sequence having an identity of not less than 80% to the sequence.

The other is a C-terminal side fragment of GDF15 propeptide formed by processing in the N-terminal side of the glutamic acid of the 74th residue of SEQ ID NO:2 in GDPP, wherein the region from the first to 73rd residues is deleted (hereinafter also referred to as "dNT73-GDPP"). More specifically, this form includes a sequence from the glutamic acid of the 74th residue to at least the aspartic acid of the 167th residue in SEQ ID NO:2, or an amino acid sequence having an identity of not less than 80% to the sequence.

The identity is preferably not less than 90%, more preferably not less than 95%. The polypeptide of the present invention may be a polypeptide having an amino acid sequence which is the same as the above sequence except that one or several amino acids are deleted, substituted, inserted, and/or added. The term "several" means preferably 2 to 20, more preferably 2 to 10, still more preferably 2 to 5.

In reducing SDS-PAGE. GDF15 propeptide is detected at a molecular weight of about 20,000; dNT57-GDPP is detected at a molecular weight of about 17,000; and dNT73-GDPP is detected at a molecular weight of about 15,000. More specifically, for example, when SDS-PAGE is carried out under reducing conditions according to a conventional method using polyacrylamide gel with a gradient of 10 to 20% by mass, they are detected at positions close to the bands corresponding to molecular weights of 20,000, 17,000, and 15,000 of molecular weight markers, preferably Precision Plus Protein Prestained Standards (manufactured by BIO-RAD).

<2> Method for Detecting Castration-resistant Prostate Cancer of Present Invention The second mode of the present invention is a method for detecting castration-resistant prostate cancer (CRPC), and includes measuring the GDF15 propeptide level in a sample. This is a method based on the characteristic presence of GDF15 propeptide in a biological sample such as blood in CRPC unlike in PCa before acquisition of castration resistance. As shown by the later-described Examples, by this method, castration-resistant prostate cancer can be detected with higher sensitivity and specificity compared to cases where a conventionally known tumor marker (PSA) or the mature body of GDF15 alone is measured.

The GDF15 propeptide measured in the present mode includes intact GDF15 propeptide, which has the amino acid sequence from the leucine of the 30th residue to the arginine of the 194th residue in the GDF15 amino acid sequence of SEQ ID NO:2 (hereinafter also referred to as "iGDPP"), and/or a GDF15 propeptide fragment. The GDF15 propeptide fragment includes dNT57-GDPP, dNT73-GDPP, and/or other peptide fragment. The intact GDF15 propeptide means the GDF15 propeptide that has not been degraded.

In the detection method of the present invention, the method for measuring the GDF15 propeptide level is not limited. Examples of the method include methods utilizing antigen-antibody reaction using an antibody that recognizes GDF15 propeptide, and methods utilizing mass spectrometry.

Specific examples of the methods utilizing antigen-antibody reaction using an antibody that recognizes GDF15 propeptide include the following.

(a) A competition method using a labeled measuring object and an antibody that recognizes the measuring object, which method utilizes competitive binding of the labeled measuring object and the measuring object contained in the sample to the antibody.

(b) A method using surface plasmon resonance, wherein the sample is brought into contact with a chip on which an antibody that recognizes the measuring object is immobilized, and a signal dependent on binding of the antibody to the measuring object is detected.

(c) A fluorescence polarization immunoassay using a fluorescently labeled antibody that recognizes measuring object, which immunoassay utilizes the phenomenon that binding of the antibody to the measuring object causes an increase in the degree of fluorescence polarization.

(d) A sandwich method using two kinds of antibodies (one of which is a labeled antibody) that recognize the measuring object at different epitopes, wherein formation of a complex of the three molecules, that is, the two antibodies and the measuring object, is allowed to occur.

(e) A method in which pretreatment is carried out by concentrating the measuring object in the sample using an antibody that recognizes the measuring object, and the polypeptide in the bound protein is detected using a mass spectrometer or the like.

Although the methods (d) and (e) are simple and versatile, the method (d) is more preferred for processing of a large number of samples since the technologies related to the reagents and the devices for this method have been sufficiently established.

As the antibody that recognizes GDF15 propeptide, an antibody that recognizes the N-terminal region of GDF15 propeptide, for example, an antibody that binds to an antigenic determinant in the region from the leucine of the 30th residue to the arginine of the 57th residue in SEQ ID NO:2 may be preferably used for measurement of the iGDPP level. Further, an antibody that recognizes the C-terminal region of GDF propeptide, for example, an antibody that binds to an antigenic determinant in the region from the glutamic acid of the 74th residue to the arginine of the 194th residue in SEQ ID NO:2 may be preferably used for measurement of the total of the iGDPP level and the GDPP fragment level (total GDPP; hereinafter also referred to as "tGDPP").

The antibody that recognizes GDF15 propeptide can be obtained by immunizing an animal using as an immunogen, for example, GDF15 propeptide itself, an oligopeptide composed of a partial region of GDF15 propeptide, or a polynucleotide encoding intact pro-GDF15 protein or a partial region thereof.

The animal to be used for the immunization is not limited as long as the animal has ability to produce antibodies. The animal may be a mammal normally used for immunization, such as mouse, rat, or rabbit, or may be a bird such as chicken.

In cases where GDF15 propeptide itself or an oligopeptide composed of a partial region of GDF15 propeptide is used as the immunogen, its structure may change during the process of preparing the protein or the oligopeptide. Therefore, in some cases, the antibody obtained may not have high specificity or binding capacity to the desired antigen, so that quantification of the amount of GDF15 propeptide contained in the sample may be inaccurate as a result. On the other hand, in cases where an expression vector containing a polynucleotide encoding intact pro-GDF15 protein or a partial region thereof is used as the immunogen, the intact GDF15 propeptide protein or the partial region thereof introduced is expressed as it is without undergoing a structural change in the body of the immunized animal. Therefore, an antibody having high specificity and binding capacity (that is, high affinity) to the GDF15 propeptide in the sample can be obtained, which is preferred.

The antibody that recognizes GDF15 propeptide may be either a monoclonal antibody or a polyclonal antibody. The antibody is preferably a monoclonal antibody.

The method of establishment of a hybridoma cell that produces an antibody that recognizes GDF15 propeptide may be appropriately selected from methods whose techniques have been established. For example, a hybridoma cell that produces a monoclonal antibody that recognizes GDF15 propeptide can be established by collecting B cells from an animal immunized by the above method, fusing the B cells with myeloma cells electrically or in the presence of polyethylene glycol, selecting a hybridoma cell that produces a desired antibody using HAT medium, and preparing the selected hybridoma cell into a monoclone by the limiting dilution method.

The selection of the antibody that recognizes GDF15 propeptide, for example, the monoclonal antibody that recognizes GDF15 propeptide, used in the method for detecting castration-resistant prostate cancer of the present invention may be carried out based on affinity to a GPI (glycosyl phosphatidyl inositol)-anchor type GDF15 propeptide or secretory GDF15 propeptide derived from a host expression system.

The host is not limited, and may be appropriately selected from microorganisms such as E. coli or yeast, insect cells, and animal cells that are usually used for protein expression by those skilled in the art. The host is preferably a mammalian cell since it enables expression of a protein having a structure similar to that of natural GDF15 propeptide by post-translational modification such as disulfide bonding or glycosylation. Examples of the mammalian cell include the human embryonic kidney (HEK)-derived 293T cell line, monkey kidney COS7 cell line, Chinese hamster ovary (CHO) cells, and cancer cells isolated from human, which are conventionally used.

The method of purification of the antibody to be used in the method for detecting castration-resistant prostate cancer of the present invention may be appropriately selected from methods whose techniques have been established. For example, after culturing hybridoma cells which are established by the above method and which produce an antibody, the culture supernatant may be collected, and the antibody may be concentrated, if necessary, by ammonium sulfate precipitation. Thereafter, by affinity chromatography using a carrier to which Protein A. Protein G, Protein L, or the like is immobilized, and/or by ion-exchange chromatography, purification of the antibody is possible.

The labeled antibody used for the antigen-antibody reaction in the sandwich method described above may be prepared by labeling an antibody purified by the above method with, for example, an enzyme such as peroxidase or alkaline phosphatase. The labeling may also be carried out using a method whose technique has been sufficiently established.

The method for detecting GDF15 propeptide and the mature body of GDF15 utilizing mass spectrometry in the detection method of the present invention is described below concretely.

In cases of a blood sample, a pretreatment step is preferably carried out by removing proteins contained in large amounts in blood such as albumin, immunoglobulin, and transferrin using Agilent Human 14 or the like, and performing further fractionation by ion exchange, gel filtration, reverse-phase HPLC, and/or the like.

The measurement can be carried out by tandem mass spectrometry (MS/MS), liquid chromatography-tandem mass spectrometry (LC/MS/MS), matrix assisted laser desorption ionization time-of-flight mass spectrometry (MALDI-TOF/MS), surface enhanced laser desorption ionization mass spectrometry (SELDI-MS), or the like.

In the detection method of the present invention, castration-resistant prostate cancer is preferably judged to be detected when the GDF15 propeptide level obtained by the measurement is higher than a reference value (cutoff value) calculated from a control.

The GDF15 propeptide level used for the judgment may be either a measured value or a converted concentration value. The converted concentration value means a value converted from a measured value based on a calibration curve prepared using GDF15 propeptide as a standard sample. The concentration of the standard sample was determined by conversion from a value measured based on a calibration curve of a standard peptide prepared by mass spectrometry.

The reference value (cutoff value) may be appropriately set to a measured value which provides optimum sensitivity and specificity, by carrying out measurement for samples free of castration-resistant prostate cancer such as samples of prostate cancer before acquisition of castration resistance, other urological cancers, benign prostatic hypertrophy, or healthy individuals, as well as samples of castration-resistant prostate cancer, and then carrying out receiver operating characteristic (ROC) curve analysis. More specifically, for example, the reference value (cutoff value) of the GDF15 propeptide level may be set to a concentration of 1.337 ng/mL when plasma is used as a sample.

<3> Reagent for Detecting Castration-Resistant Prostate Cancer of Present Invention The third mode of the present invention is a reagent for detecting castration-resistant prostate cancer, the reagent comprising an antibody that recognizes GDF15 propeptide. In other words, the present mode is use of an antibody that recognizes GDF15 propeptide or a reagent containing it, in detection of castration-resistant prostate cancer.

The antibody is usually an antibody that binds to an antigenic determinant in the region from the leucine of the 30th residue to the arginine of the 194th residue in the pro-GDF15 represented by SEQ ID NO:2.

The GDF15 propeptide to be detected in the present mode includes intact GDF15 propeptide and/or a GDF15 propeptide fragment. The GDF15 propeptide fragment includes dNT57-GDPP, dNT73-GDPP, and other peptide fragment.

In cases where the reagent of the present invention is used in the sandwich method described above, the reagent needs to contain, as the antibody, two kinds of antibodies for different epitopes.

The detection reagent of the present invention may further contain a detection reagent for a tumor marker for prostate cancer containing an antibody that recognizes the tumor marker for prostate cancer. Examples of the tumor marker for prostate cancer include PSA.

The antibody contained in the reagent of the present invention may be an antibody itself, a labeled antibody, or an antibody immobilized on a solid phase.

The reagent of the present invention is described below concretely for cases where it is used for a two-step sandwich method, which is one mode of the sandwich method described above. However, the present invention is not limited thereto.

The reagent of the present invention can be prepared by the method described in the following (I) to (III).

(I) First, Antibody 1, one of the two kinds of antibodies for different epitopes to be used in the sandwich method that recognize GDF15 propeptide (hereinafter referred to as "Antibody 1" and "Antibody 2"), is bound to a carrier capable of B/F (Bound/Free) separation such as an immunoplate or magnetic particles. The binding method may be either physical binding utilizing hydrophobic bonding, or chemical bonding using a linker reagent capable of cross-linking two substances to each other.

(II) After the binding of the Antibody 1 to the carrier, the carrier surface is subjected to blocking treatment using bovine serum albumin, skim milk, a commercially available immunoassay blocking agent, or the like for preventing non-specific binding, to provide a primary reagent.

(III) After labeling the other antibody, Antibody 2, a solution containing the obtained labeled antibody is provided as a secondary reagent. Preferred examples of the substance with which Antibody 2 is labeled include enzymes such as peroxidase and alkaline phosphatase; substances detectable with detection devices, such as fluorescent substances, chemiluminescent substances, and radioisotopes; and substances to which another molecule specifically binds, such as biotin, to which avidin specifically binds. Preferred examples of the solution for the secondary reagent include buffers with which antigen-antibody reaction can be favorably carried out, such as phosphate buffer and Tris-HCl buffer.

The thus prepared reagent of the present invention may be freeze-dried, if necessary.

In cases of a one-step sandwich method, binding of Antibody 1 to the carrier and subsequent blocking treatment may be carried out in the same manner as in (I) and (II), and a buffer containing a labeled Antibody 2 may be further added to the antibody-immobilized carrier, to prepare a reagent.

For detection and measurement of GDF15 propeptide by a two-step sandwich method using the reagent obtained by the method described above, the method described in the following (IV) to (VI) may be carried out.

(IV) The primary reagent prepared in (II) is brought into contact with a sample for a predetermined period of time at a constant temperature. In terms of the reaction conditions, the reaction may be carried out at a temperature within the range of 4° C. to 40° C. for 5 minutes to 180 minutes.

(V) Unreacted substances are removed by B/F separation, and then the secondary reagent prepared in (III) is brought into contact with the reaction product for a predetermined period of time at a constant temperature to allow formation of a sandwich complex. In terms of the reaction conditions, the reaction may be carried out at a temperature within the range of 4° C. to 40° C. for 5 minutes to 180 minutes.

(VI) Unreacted substances are removed by B/F separation, and the labeling substance of the labeled antibody is quantified. Based on a calibration curve prepared using a GDF15 propeptide solution having a known concentration as a standard, the concentration of human GDF15 propeptide in the sample is quantified.

Also for the mature body of GDF15, a detection reagent can be prepared by the above method. A detection reagent for the mature body of GDF15 is applicable also as a detection reagent for a tumor marker for prostate cancer. The detection reagent for a tumor marker for prostate cancer may be one prepared in the same manner as the reagent of the present invention described above, or may be a commercially available product.

The amount of each reagent component such as the antibody contained in the detection agent may be appropriately set depending on conditions such as the amount of the sample, the type of the sample, the type of the reagent, and the detection method. More specifically, for example, in cases where the GDF15 propeptide level is measured as described below by a sandwich method using 50 μL of 2.5-fold diluted serum or plasma as a sample, the amount of the antibody to be bound to the carrier may be 100 ng to 1000 μg, and the amount of the labeled antibody may be 2 ng to 20 μg in a reaction system in which 50 μL of the sample is reacted with the antibodies.

The detection reagent for castration-resistant prostate cancer of the present invention is applicable to either manual detection or detection using an automatic immunodiagnostic apparatus. Detection using an automatic immunodiagnostic apparatus is especially preferred since it enables the detection without being affected by endogenous measurement-inhibiting factors and competing enzymes contained in the sample, and also enables rapid quantification of the concentrations of GDF15 propeptide and tumor markers for castration-resistant prostate cancer in the sample.

Examples of the sample (test sample) to be subjected to the method for detecting castration-resistant prostate cancer of the present invention and the detection reagent of the present invention include blood components such as whole blood, blood cells, serum, and plasma; extracts from cells and tissues; urine; and cerebrospinal fluid. A blood component or a body fluid such as urine is preferably used as the sample since it allows simple noninvasive detection of castration-resistant prostate cancer. From the viewpoint of simplicity of sample collection and versatility for other test items, use of a blood component as the sample is especially preferred. The dilution rate of the sample may be appropriately selected from no dilution to 100-fold dilution depending on the type and the conditions of the sample used. For example, 50 μL of a 2.5-fold diluted sample may be used in cases of serum or plasma.

In cases where clinical evaluation of castration-resistant prostate cancer is carried out by a method in which the GDPP level is measured, the method is more preferably a method in which iGDPP in plasma is measured as described in the later-mentioned Examples.

The method for detecting castration-resistant prostate cancer of the present invention and the detection reagent of the present invention are useful also for follow-up of CRPC patients after acquisition of castration resistance. In particular, they are expected to allow accurate reflection of the disease state because of, for example, reduced false positivity relative to an existing prostate cancer marker PSA.

EXAMPLES

Examples are shown below for concrete description of the present invention. However, these Examples merely show examples of the present invention, and the present invention is not limited by the Examples.

<Example 1> Proteome Analysis of Secretory Protein of Urological Cancer Cell Lines First, in order to search for proteins characteristically produced in castration-resistant prostate cancer, comprehensive analysis of secretory protein of cultured urological cancer cell lines was carried out. Each of CRPC cell lines 22Rv. PC3, and LnCap-AI, and, as controls for comparison, prostate cancer cell lines LnCap, VCap, and DU145, bladder cancer cell lines 5637, T24, TCC, and UMUC3, and renal cancer cell lines CAKI, ACHN, 786-0, and U3, was cultured in RPMI 1640 medium supplemented with 10% fetal bovine serum in a 150-mm diameter culture dish. Twenty-four hours later, the medium was replaced with 20 mL of RPMI 1640 medium (serum-free medium) supplemented with 4.0 nM epidermal growth factor (manufactured by Sigma). After two days of additional culture, the medium was filtered through a 0.22-μm filter, and then freeze-dried. Powder of the culture supernatant obtained was dissolved in 30 mM Tris-HCl buffer (pH 8.5) supplemented with 7 M urea, 2 M thiourea, and 4% CHAPS. The culture supernatant was then desalted and concentrated by acetone precipitation, and then redissolved in 10 mM ammonium bicarbonate solution containing 1% RapiGest as a surfactant. The obtained protein sample was subjected to reductive alkylation and trypsin digestion according to conventional methods. The peptide fragments obtained were subjected to measurement using a nano-LC-LTQ Orbitrap mass spectrometer (manufactured by Thermo Fisher Scientific Inc.). The obtained data were analyzed using Protein Discoverer 1.3 software (manufactured by Thermo Fisher Scientific Inc.), and proteins were identified by performing search against amino acid sequences in the Swiss-Prot database.

The proteins identified from the prostate cancer-derived cell lines included PSA and PAP, which are existing markers for prostate tumor. The propeptide portion of GDF15 was characteristically detected in the culture supernatants of all prostate cancer cell lines except DU145 (FIG. 1).

<Example 2> Preparation of Monoclonal Antibodies

By a known method (DNA immunization, JP 2013-061321 A), 10 kinds each of monoclonal antibodies that recognize GDF15 propeptide or the mature body of GDF15 were prepared.

<Example 3> Epitope Analysis of Monoclonal Antibodies

The antigen recognition site of each antibody prepared in Example 2 was identified using culture supernatants of cells expressing intact GDF15 propeptide (iGDPP) and N-terminal deletion variants of the GDF15 propeptide fragment (dNT-GDPP).

For expression evaluation and the purification process of each recombinant GDPP, a FLAG tag and a Strep II tag were inserted into the 5'-end, and an oligonucleotide encoding BNC peptide (JP 2009-240300 A), which is composed of the seven amino acids in the C-terminal side of BNP (brain natriuretic peptide), was inserted into the 3'-end, to prepare plasmids capable of expressing secretory iGDPP and four kinds of dNT-GDPP. FIG. 2A shows the structures of the recombinant GDPPs prepared. The preparation method is described below more concretely.

(1) Using primers designed based on cDNA of human GDF15 (GenBank Accession No.: NM_004864) with the combinations shown in Table 1, polynucleotides corresponding to iGDPP, dNT37-GDPP, dNT59-GDPP, dNT-77GDPP, and dNT94-GDPP were amplified by RT-PCR according to a conventional method.

TABLE 1

| Recombinant GDPP | Forward primer | Reverse primer |
|---|---|---|
| Secretory iGDPP | SEQ ID NO: 3: The 15 bases in the 3'-end correspond to the base sequence of positions 120 to 134 in SEQ ID NO: 1. | SEQ ID NO: 4: The 15 bases in the 5'-end correspond to the base sequence of positions 585 to 599 in SEQ ID NO: 1. |
| Secretory dNT37-GDPP | SEQ ID NO: 5: The 17 bases in the 3'-end correspond to the base sequence of positions 144 to 160 in SEQ ID NO: 1. | |
| Secretory dNT59-GDPP | SEQ ID NO: 6: The 15 bases in the 3'-end correspond to the base sequence of positions 207 to 221 in SEQ ID NO: 1. | |
| Secretory dNT77-GDPP | SEQ ID NO: 7: The 16 bases in the 3'-end correspond to the base sequence of positions 261 to 276 in SEQ ID NO: 1. | |
| Secretory dNT94-GDPP | SEQ ID NO: 8: The 15 bases in the 3'-end correspond to the base sequence of positions 115 to 229 in SEQ ID NO: 1. | |

(2) Into the HindIII-EcoRI site of pFLAG1 (manufactured by SIGMA), which is a plasmid containing the GPI anchor region of placental alkaline phosphatase, each RT-PCR amplification product of (1) was inserted using In-fusion (manufactured by Clontech) according to its protocol, to construct each secretory-GDPP expression plasmid.

(3) In order to confirm that each secretory GDPP expressed from the polynucleotide inserted in the plasmid pFLAG1 has the FLAG tag in the N-terminal side and the BNC tag in the C-terminal side, a test was carried out by the following method using the 293T cell line, which is a transiently expressing cell.

(3-1) According to a conventional method, each secretory GDPP expression plasmid constructed in (2) was introduced into the 293T cell line, and each secretory GDPP was transiently expressed. The culture liquid after 72 hours of culture was centrifuged, and the resulting supernatant was collected as each secretory GDPP solution.

(3-2) Using each secretory GDPP solution as a sample, (A) an enzyme immunoassay (ELISA) and (B) Western blotting (WB) were carried out.

(A) ELISA (A-1) A rabbit anti-FLAG polyclonal antibody (manufactured by ROCKLAND) was diluted with carbonate buffer (pH 9.8) such that its amount became 100 ng/well, and then immobilized on a MaxiSorp 96-well plate (manufactured by NUNC).

(A-2) After allowing the reaction to proceed at 4° C. overnight, the plate was washed three times with TBS (Tris-Buffered Saline), and TBS solution supplemented with 3% bovine serum albumin (BSA) was added to each well at 250 µL/well. The plate was then left to stand at room temperature for 2 hours.

(A-3) The plate was then washed three times with TBS. Each secretory GDPP solution and, as a negative control, culture supernatant of the 293T cell line to which no expression plasmid was introduced were added thereto at 50 µL/well. The plate was then left to stand at room temperature for 1 hour.

(A-4) After washing the plate three times with TBS supplemented with 0.5% Tween 20 (TBS-T), a mouse anti-BNC monoclonal antibody solution diluted to 1 µg/mL with TBS-T supplemented with 1% BSA (1% BSA/TBS-T) was added to the plate at 50 µL/well. The plate was then left to stand at room temperature for 1 hour.

(A-5) After washing the plate three times with TBS-T, a horseradish peroxidase (HRP)-labeled anti-mouse immunoglobulin G-Fc antibody (manufactured by SIGMA) solution 10,000-fold diluted with 1% BSA/TBS-T was added to the plate at 50 µL/well, and the plate was then left to stand at room temperature for 1 hour.

(A-6) After washing the plate four times with TBS-T, TMB Microwell Peroxidase Substrate (manufactured by KPL) was added to the plate, and the reaction was stopped with 1 moL phosphoric acid solution, followed by measuring the absorbance at 450 nm using an absorbance measurement plate reader.

(B) Western Blotting (B-1) Each secretory GDPP solution obtained in (3-1) and, as a negative control, culture supernatant of the 293T cell line to which no expression plasmid was introduced were developed by SDS-PAGE according to a conventional method, and transferred to a PVDF membrane (manufactured by BioRad).

(B-2) The membrane was blocked with Blocking One solution (manufactured by Nacalai Tesque), and then an alkaline phosphatase-labeled anti-BNC antibody was added to the blocking solution at 1 µg/sheet, followed by allowing the reaction to proceed at 4° C. overnight.

(B-3) After washing with TBS-T, ECL Select Reagent (manufactured by GE Healthcare) was used, and the obtained chemiluminescence was detected using a LAS 4000 image analyzer (manufactured by GE Healthcare).

In comparison with the negative control (culture supernatant of 293T), each secretory GDPP solution (secretory GDPP culture supernatant) showed a clear signal in a manner dependent on the amount added. Thus, production of each secretory GDPP into the culture supernatant could be confirmed.

Each secretory GDPP solution (culture supernatant of secretory GDPP) showed clear bands near molecular weights of about 27,000, about 20,000, and about 18,000. Thus, production of secretory GDPP having the FLAG tag in the N-terminus and the BNC tag in the C-terminus into the culture supernatant could be confirmed.

Figure 2B:
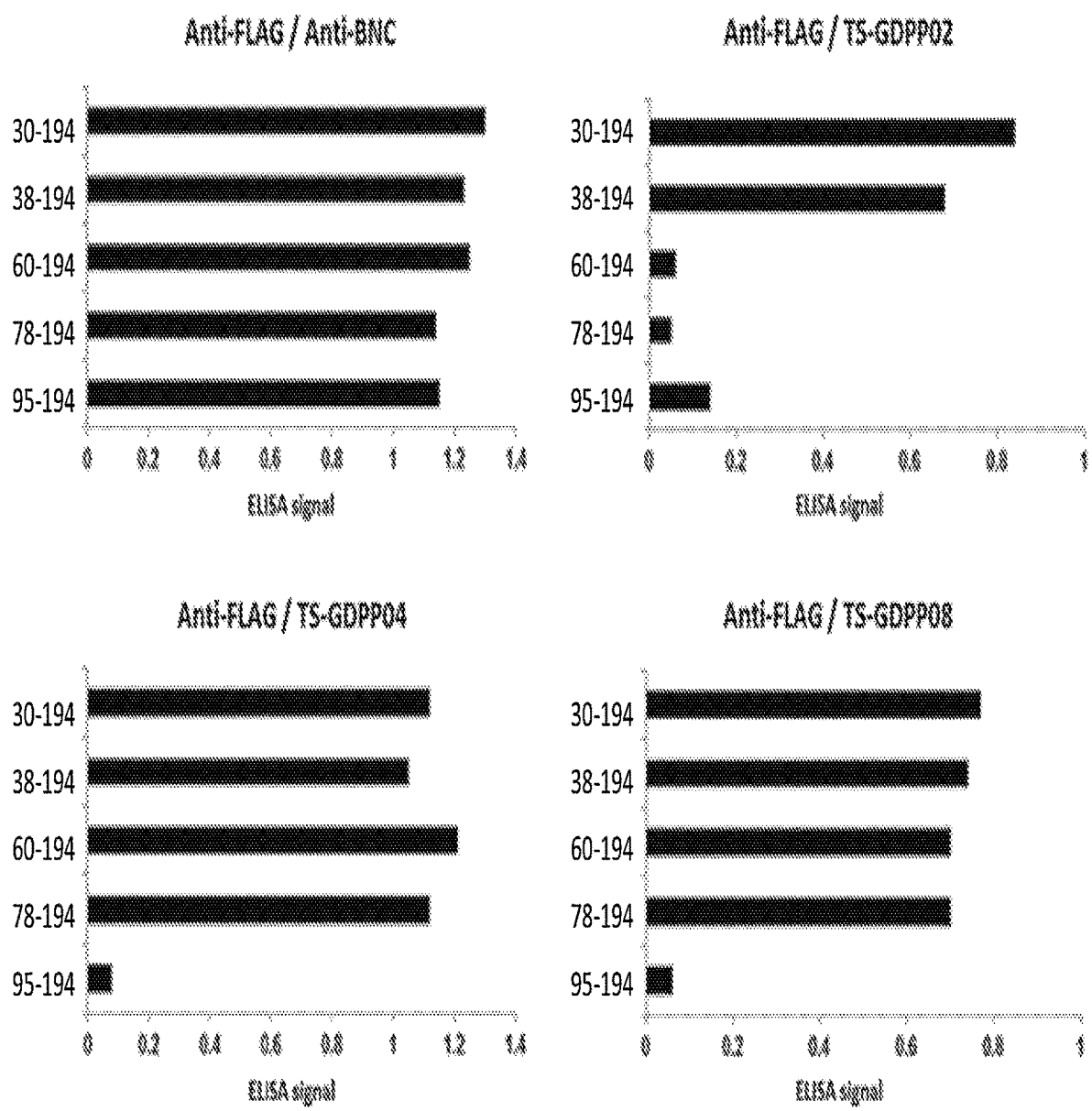
FIG. 2B is a diagram illustrating the result of epitope analysis of each monoclonal antibody by ELISA. The abscissa represents the absorbance.

By the ELISA method described above, reactions of the five kinds of recombinant GDPP culture supernatant with each monoclonal antibody was evaluated. Table 2 shows the antigen recognition site of each antibody revealed from the results of the ELISA analysis shown in FIG. 2B.

TABLE 2

| Antibody No. | Antigen recognition site |
| --- | --- |
| TS-GDPP02 | 38-58 aa |
| TS-GDPP03 | 78-95 aa |
| TS-GDPP04 | |
| TS-GDPP06 | |
| TS-GDPP08 | |

<Example 4> Evaluation of Immunoprecipitability Using Magnetic Beads on Which Monoclonal Antibodies are Immobilized Antibody-immobilized magnetic particles wherein the 10 kinds of GDF15 propeptide monoclonal antibodies prepared in Example 2 and a rabbit anti-FLAG polyclonal antibody (manufactured by ROCKLAND) are immobilized were prepared, and proteins in the culture supernatants of secretory GDF15 propeptide and the culture supernatants of prostate cancer cells that specifically bind to the antibodies were identified by the following method. As the prostate cancer cells, LnCap, PC3, and DU145 were used.

(1) Part of the purified monoclonal antibodies prepared in Example 2 were immobilized on Dynabeads M-280 Tosylactivated magnetic particles (manufactured by Invitrogen) according to a conventional method, and blocking was carried out with PBS supplemented with 0.5% BSA, to prepare antibody-immobilized magnetic particles.

(2) Immunoprecipitation-Western Blotting Method (IP-WB Method)

(2-1) The three kinds of cancer cells were cultured in RPMI 1640 medium (manufactured by Wako Pure Chemical Industries, Ltd.) supplemented with 10% fetal bovine serum at 100% confluence for three days.

(2-2) After centrifugation of the culture supernatant, each of the 10 kinds of antibody-immobilized magnetic particles were added to 0.1 mL of the supernatant, and the resulting mixture was stirred at room temperature for 1 hour to allow the reaction to proceed.

(2-3) The particles were then washed twice with PBST-NP40 (0.1% Tween 20, 1% NP40), and then three times with PBS that does not contain a surfactant.

(2-4) Proteins bound to each kind of antibody-immobilized magnetic particles were analyzed by the Western blotting described in Example 3 (B). As molecular weight markers, Full-Range Rainbow Molecular Weight Markers (manufactured by GE) were used. As the gel for the SDS-PAGE, a 10 to 20% gradient gel (manufactured by Marysol) was used. As a detection antibody in the Western blotting, an anti-BNC antibody labeled using an alkaline phosphatase labeling kit (manufactured by Dojindo Laboratories) was used.

<Example 5> Identification of Monoclonal Antibody-Bound Proteins by Mass Spectrometry Further study by IP was carried out using magnetic particles on which the TS-GDPP02 antibody, TS-GDPP04 antibody, and TS-GDPP08 antibody, which were found to have high affinity to GDF15 propeptide in Example 4, are immobilized. Polypeptides of GDF15 propeptide that bind to the TS-GDPP02 antibody and the TS-GDPP04 antibody were analyzed by mass spectrometry. Using the LnCap used in Example 1 as a prostate cancer culture supernatant, a sample for the mass spectrometry was prepared as follows.

(1) The LnCap sample solution was subjected to IP with the three kinds of antibody-immobilized magnetic particles by the method described in Example 4, and then elution was carried out with SDS Loading Buffer according to a conventional method. The LnCap supernatant before the IP, the LnCap supernatant after the IP, and the IP products were developed by SDS-PAGE, and the separated proteins were stained by SYPRO-Ruby staining (manufactured by Invitrogen).

Figure 3A:
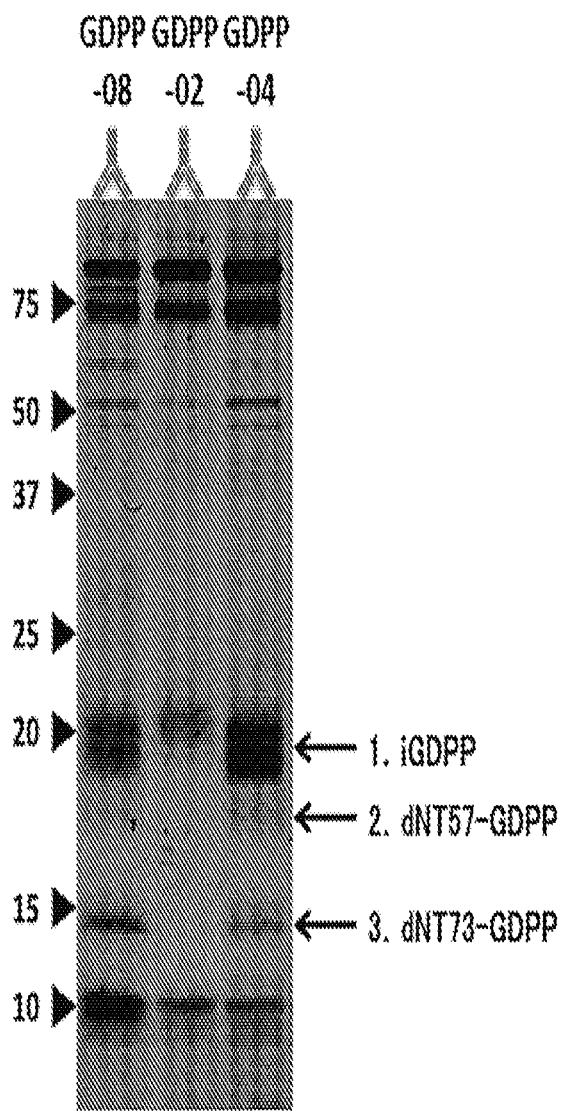
FIG. 3A is a diagram (Ruby-stained image) (photograph) illustrating the result of development, by SDS-PAGE, of IP products obtained from LnCap supernatant using three kinds of monoclonal antibodies.

(2) A total of three kinds of fragments corresponding to the stained bands with molecular weights of about 20,000, about 17,000, and about 15,000 (corresponding to the positions 1, 2, and 3 in the SYPRO-Ruby-stained image shown in FIG. 3A) were excised, and subjected to reductive alkylation using dithiothreitol and iodoacetamide, followed by carrying out in-gel digestion with trypsin.

(3) The peptide fragments produced by the trypsin digestion were separated by MS/MS measurement using a nano-LC-LTQ Orbitrap mass spectrometer (manufactured by Thermo Fisher Scientific Inc.) with a C18 reverse-phase column. The obtained data were analyzed using Protein Discoverer 1.3 software (manufactured by Thermo Fisher Scientific Inc.), and proteins were identified by performing search against amino acid sequences in the Swiss-Prot database.

Figure 3B:
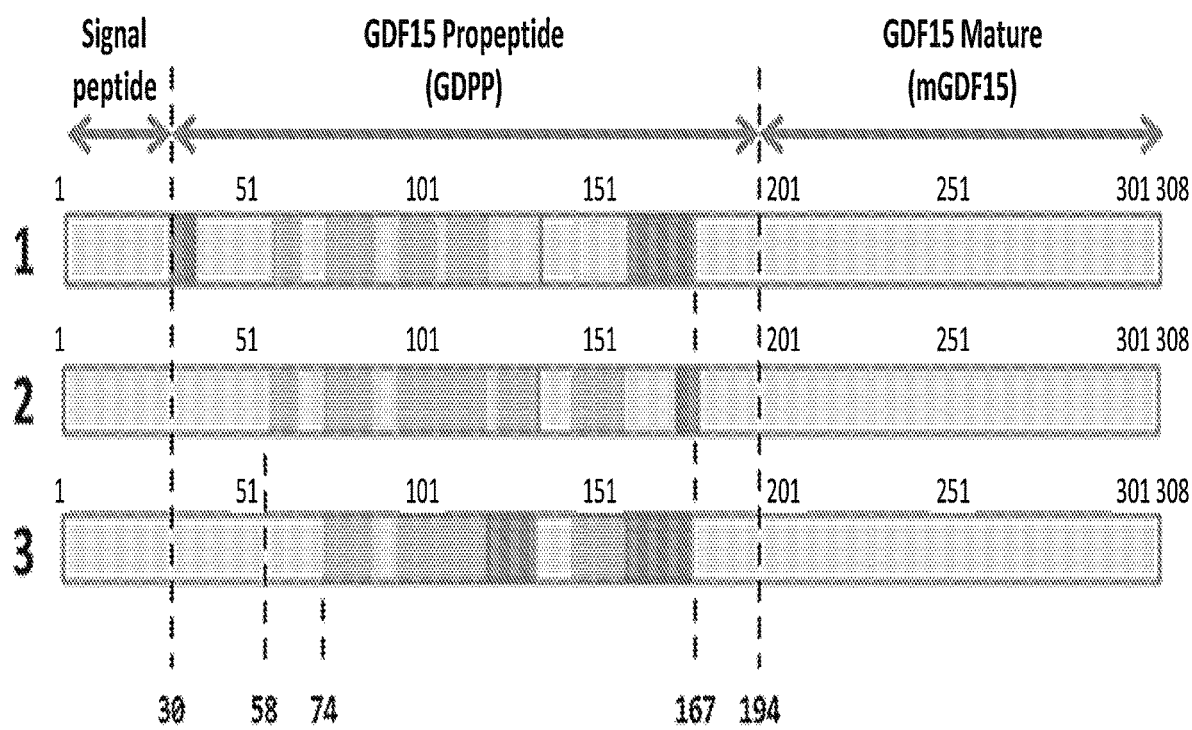
FIG. 3B is a diagram illustrating the GDPP peptide detected, using a mass spectrometer, from the sample excised from each band of SDS-PAGE.

The Ruby-stained image is shown in FIG. 3A, and the peptides identified from the IP products of LnCap having molecular weights of about 20,000, about 17,000, and about 15,000 are shown in FIG. 3B (the dark gray portions correspond to the regions detected by the mass spectrometry). In the Ruby-stained image, signals that were assumed to be derived from GDF15 propeptide were found for the TS-GDPP04 antibody and the TS-GDPP08 antibody at molecular weights of about 20,000, about 17,000, and about 15,000. On the other hand, only the signal at a molecular weight of about 20,000 was detected for the TS-GDPP02 antibody, which recognizes the N-terminal region.

By the mass spectrometry data of the LnCap IP products, it was demonstrated that the proteins with molecular weights of about 20,000, about 17,000, and about 15,000 positioned at 1, 2, and 3 in the Ruby-stained image are GDF15 propeptides. The GDF15 propeptides positioned at 2 and 3 in the Ruby-stained image were found to be N-terminus-deleted GDF15 propeptide fragments (dNT57-GDPP and dNT73-GDPP) formed by fragmentation due to deletion of the region from the N-terminus to the arginine of the 57th residue or to the leucine of the 73rd residue, respectively, in SEQ ID NO:2. Regarding the C-terminus, sensitive detection was possible for the region to the aspartic acid of the 167th residue in SEQ ID NO:2 in any type of GDPP. Although detection of dNT57-GDPP was possible for the region to the leucine of the 170th residue, this could be due to variation among measurements. It is thought that accurate identification of the terminus in the C-terminal region of GDPP by mass spectrometry is especially difficult since the region is arginine-rich. From these results, it is thought that the C-terminal sequence of GDPP and dNT-GDPP includes a sequence to at least the aspartic acid of the 167th residue in SEQ ID NO:2.

<Example 6> Preparation of GDF15 Propeptide Assay Reagents

Using the anti-GDPP monoclonal antibodies prepared in Example 2, two kinds of GDPP measurement reagents were prepared with different combinations of the antibodies. One of the reagents is based on combination of an antibody that recognizes the N-terminal region (TS-GDPP02) and an antibody that recognizes the C-terminal region (TS-GDPP4) of GDPP, and detects intact GDPP (iGDPP). The other is based on combination of antibodies that recognize the C-terminal region (TS-GDPP04 and TS-GDPP08), and detects both iGDPP and dNT-GDPP. The value detected by the latter reagent is defined as total GDPP (tGDPP). The preparation method is described below more concretely.

(1) Physical adsorption of an anti-GDF15 propeptide monoclonal antibody (TS-GDPP02 or 08) to water-insoluble ferrite carriers was allowed at room temperature for one day and night such that the adsorption occurred at 100 ng/carrier, and blocking was then carried out with 100 mM Tris buffer (pH 8.0) supplemented with 1% BSA at 40° C. for 4 hours, to prepare anti-GDF15 propeptide antibody-immobilized carriers.

(2) A labeled anti-GDF15 propeptide antibody was prepared with an anti-GDF15 propeptide monoclonal antibody (TS-GDPP04) using an alkaline phosphatase labeling kit (manufactured by Dojindo Laboratories).

(3) In each of magnetic force-permeable containers (capacity, 1.2 mL), 12 antibody-immobilized carriers prepared in (1) were placed, and 50 µL of a buffer (Tris buffer supplemented with 3% BSA, pH 8.0) containing 0.5 µg/mL of the labeled antibody prepared in (2) was added thereto, followed by carrying out freeze-drying to prepare GDF15 propeptide assay reagents. The GDF15 propeptide assay reagents prepared were tightly closed and sealed under nitrogen gas, and stored at 4° C. until the assay.

An assay reagent for the mature body of GDF15 (mGDF15) was similarly prepared using anti-mGDF15 monoclonal antibodies prepared in Example 2 (the TS-mGD18 antibody and the TS-mGD20 antibody).

<Example 7> Preparation of GDF15 Propeptide Standard Product

Since there is no commercially available product of GDF15 propeptide, the secretory iGDPP prepared in Example 3 was used as a standard product. Regarding the mature body of GDF15, a commercially available recombinant protein (R&D system) was used.

Figure 4:
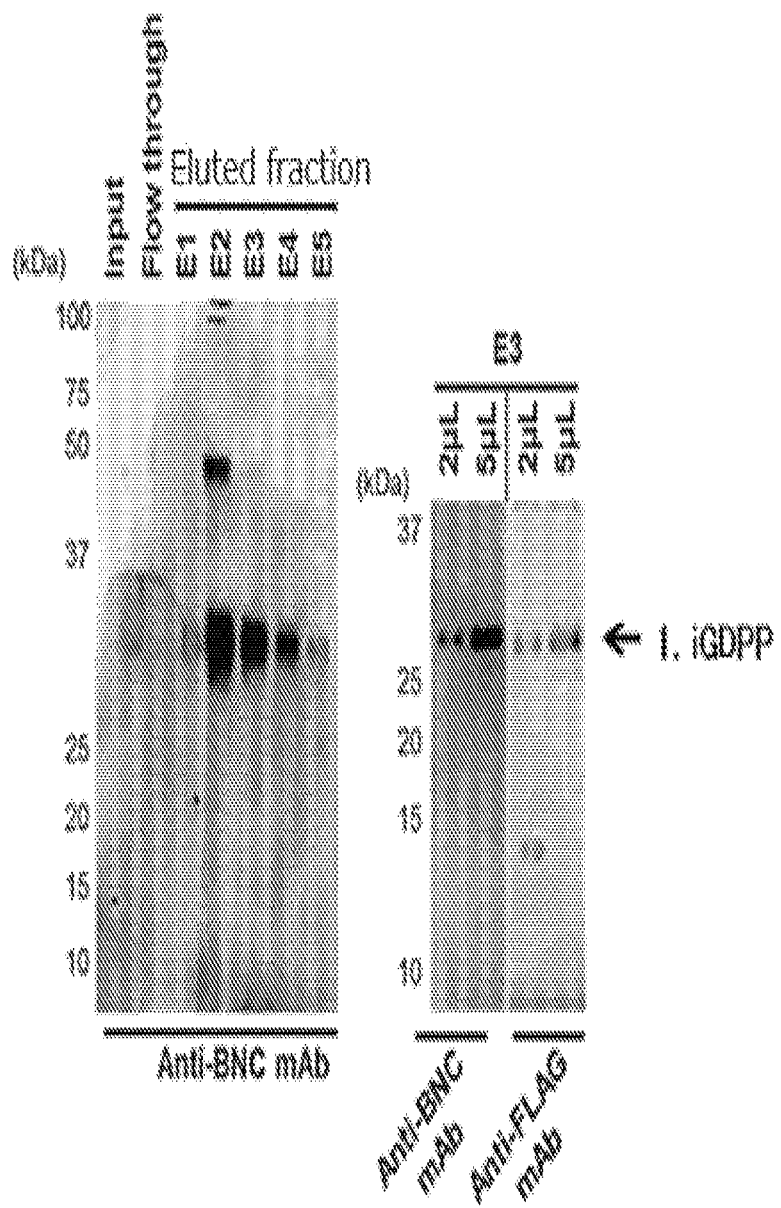
FIG. 4 is a diagram illustrating the result of purification of a recombinant iGDPP as investigated by Western blotting (photographs).

However, since degradation products are present also in the recombinant iGDPP, accurate quantification is impossible when the recombinant iGDPP is used as it is. Therefore, full-length GDF15 propeptide alone was purified using a commercially available purification kit (manufactured by IBA) by utilization of the Strep-II tag (manufactured by IBA) in the N-terminal side of the recombinant iGDPP. The secretory iGDPP after the purification was evaluated by the Western blotting described in Example 3. The result of the Western blotting of the purified GDPP product is shown in FIG. 4. Since the purified product has the tag peptide, it has a larger molecular weight. A single band corresponding to full-length GDF15 propeptide was detected by use of either an N-terminal tag antibody or a C-terminal tag antibody.

<Example 8> Evaluation of GDF15 Propeptide Standard Product

The full-length GDF15 propeptide prepared in Example 7 was subjected to quantification by mass spectrometry by the following procedure.

Figure 5:
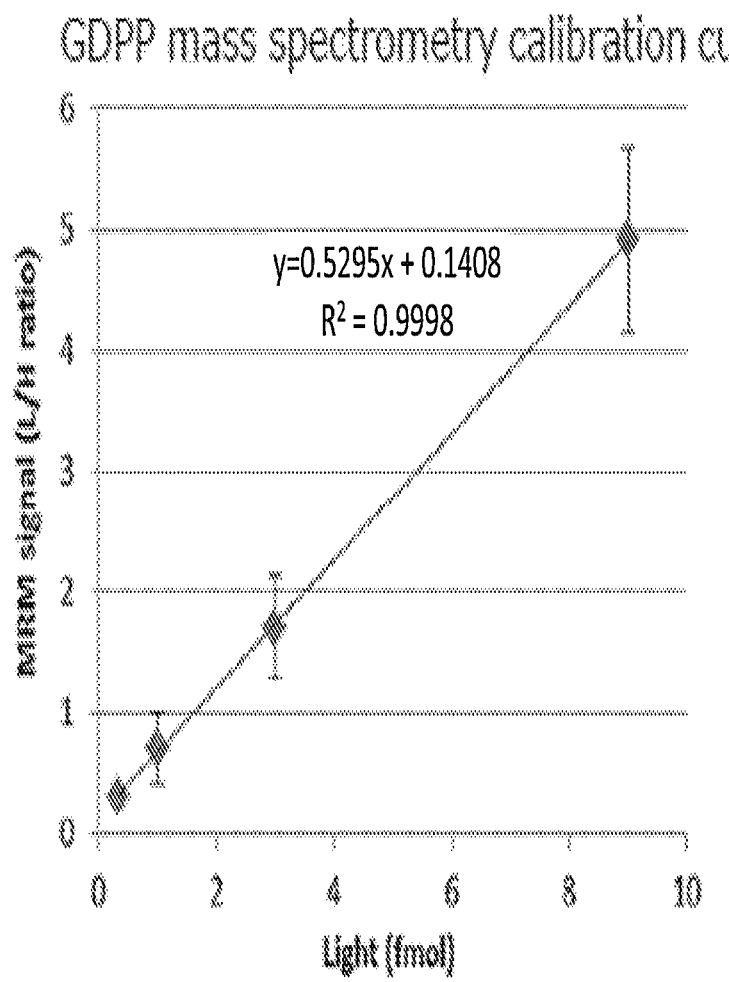
FIG. 5 is a diagram illustrating a GDPP calibration curve for quantification by MRM using a synthetic peptide.

Using a synthetic peptide labeled with a stable isotope (Heavy peptide, manufactured by Sigma-Aldrich) and an unlabeled synthetic peptide (Light peptide, manufactured by Sigma-Aldrich), a calibration curve based on the concentration and the L/H signal ratio was prepared (FIG. 5).

The purified GDF15 propeptide standard product prepared in Example 7 was subjected to immunoprecipitation by the method shown in Example 4 using the magnetic particles of a rabbit anti-FLAG polyclonal antibody (manufactured by ROCKLAND) prepared in Example 4. According to a conventional method, GDF15 propeptide was eluted from the antibody magnetic particles with Glycine-HCl (pH 2.5). The eluted sample was subjected to pretreatment for mass spectrometry measurement by the method described in Example 5.

Heavy peptide was added to the pretreated sample, and LC-MRM (Multiple Reactive Monitoring) measurement was carried out using a QTRAP5500 (manufactured by AB SCIEX) mass spectrometer. The obtained data were analyzed using Skyline Software. The signal ratio to Heavy peptide was compared with the calibration curve shown in FIG. 5 to determine the concentration of the recombinant iGDPP.

<Example 9> Evaluation of Performances of GDF15 Propeptide Assay Reagents

The recombinant GDPP supernatant prepared in Example 3 and the LnCap prepared in Example 5 were diluted 10-fold with FBS to provide samples containing GDF15 propeptide, and FBS alone was provided as a sample containing no GDF15, thereby providing a total of three pseudosamples. By performing five-point measurement using the two kinds of GDF15 propeptide assay reagents prepared in Example 6, the reagents were evaluated.

As an evaluation apparatus, a fully automatic enzyme immunoassay apparatus AIA-1800 (manufactured by Tosoh Corporation; manufacturing/marketing notification number, 13B3X90002000002) was used. Measurement using the fully automatic enzyme immunoassay apparatus AIA-1800 was carried out by:

(1) automatically dispensing 20 µL of a diluted sample and 80 µL of a diluent containing a surfactant to a container storing a GDF15 propeptide assay reagent prepared in Example 6;

(2) carrying out antigen-antibody reaction at a constant temperature of 37° C. for 10 minutes:

(3) carrying out eight times of washing using a buffer containing a surfactant; and (4) adding 4-methylumbelliferyl phosphate.

The concentration of 4-methylumbelliferone produced by alkaline phosphatase per unit time was provided as the measured value (nmol/(L s)).

As a result of the AIA measurement, any of the pseudosamples excluding FBS showed a coefficient of variation of not more than 3% in the five-point measurement. It was thus demonstrated that results obtained with the GDF15 propeptide assay reagents prepared in Example 6 are reliable.

Figure 6:
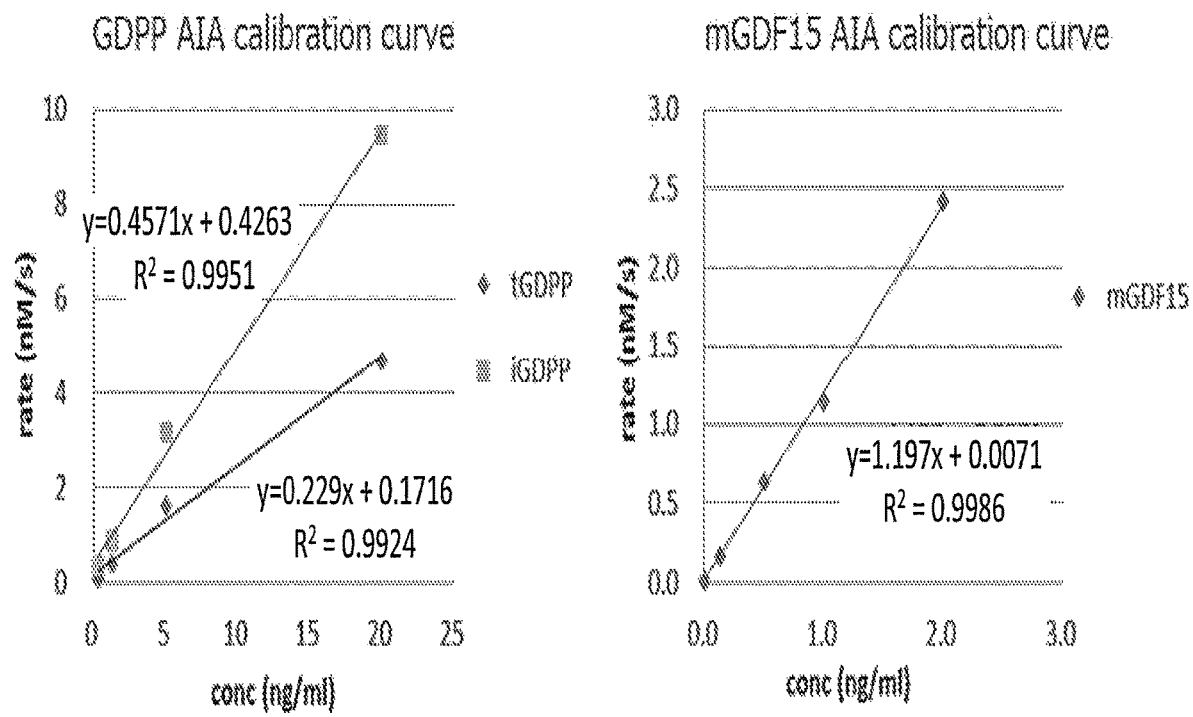
FIG. 6 is a diagram illustrating calibration curves prepared using assay reagents for iGDPP, tGDPP, and mGDF15.

The purified iGDPP whose concentration was determined in Example 8 and a commercially available mGDF15 were diluted with FBS to provide the calibration curves shown in FIG. 6 for the AIA measurement. The GDPP quantification values in the following clinical evaluation and the like were calculated based on these calibration curves.

<Example 10> Measurement of GDF15 Propeptide and Mature Body of GDF15 in Prostate Cancer Samples The sample panel (56 cases using serum and 85 cases using plasma) used in the present Example is shown in Table 3. The samples are serum and plasma samples collected by the same protocol in the department of urology, Yokohama City University. The collection was carried out with informed consent and approval by the ethical committee of Yokohama City University.

TABLE 3

| Disease | Number of cases | |
|---|---|---|
| | Serum | Plasma |
| Benign prostatic hypertrophy (BPH) | 17 | 28 |
| Prostate cancer (PCa) | 19 | 30 |
| Castration-resistant prostate cancer (CRPC) | 20 | 27 |
| Total | 56 | 85 |

Using a fully automatic enzyme immunoassay apparatus AIA-1800 (manufactured by Tosoh Corporation) as an apparatus for the evaluation, measurement was carried out using the iGDPP, tGDPP, and mGDF15 assay reagents prepared in Example 6. As comparison data, measured values of PSA (values immediately before the date of blood collection) of the samples were collected from clinical records provided by the department of urology, Yokohama City University.

Figure 7A:
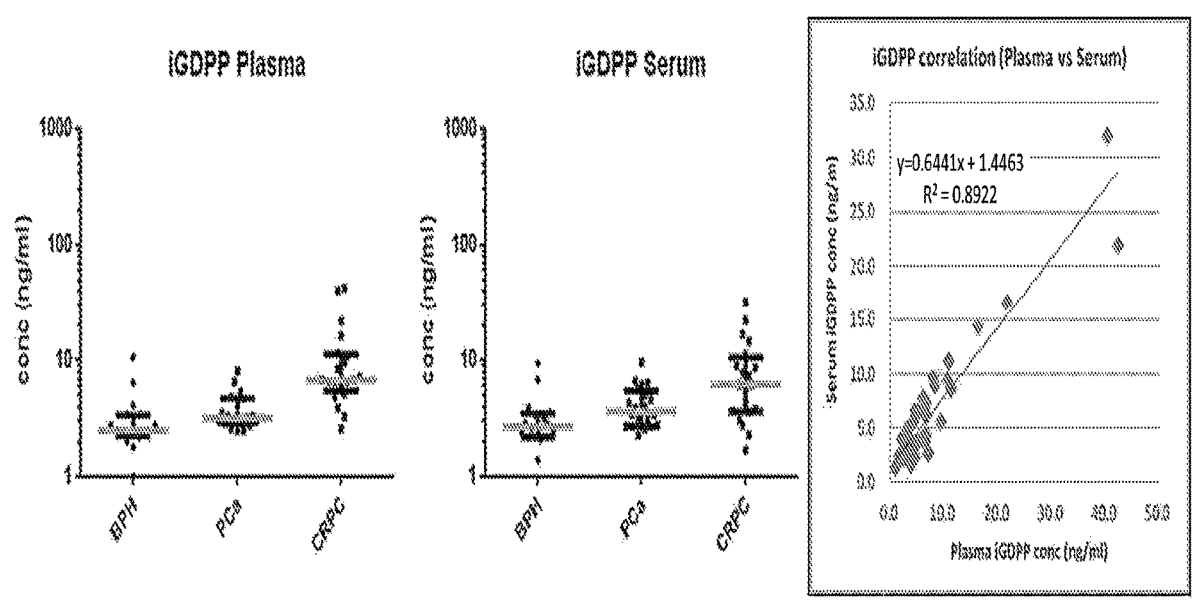
FIG. 7A is a diagram illustrating the results of AIA analysis of serum and plasma iGDPP in each prostate disease panel, and their correlations. Each horizontal bar represents the median in each disease group.
Figure 7B:
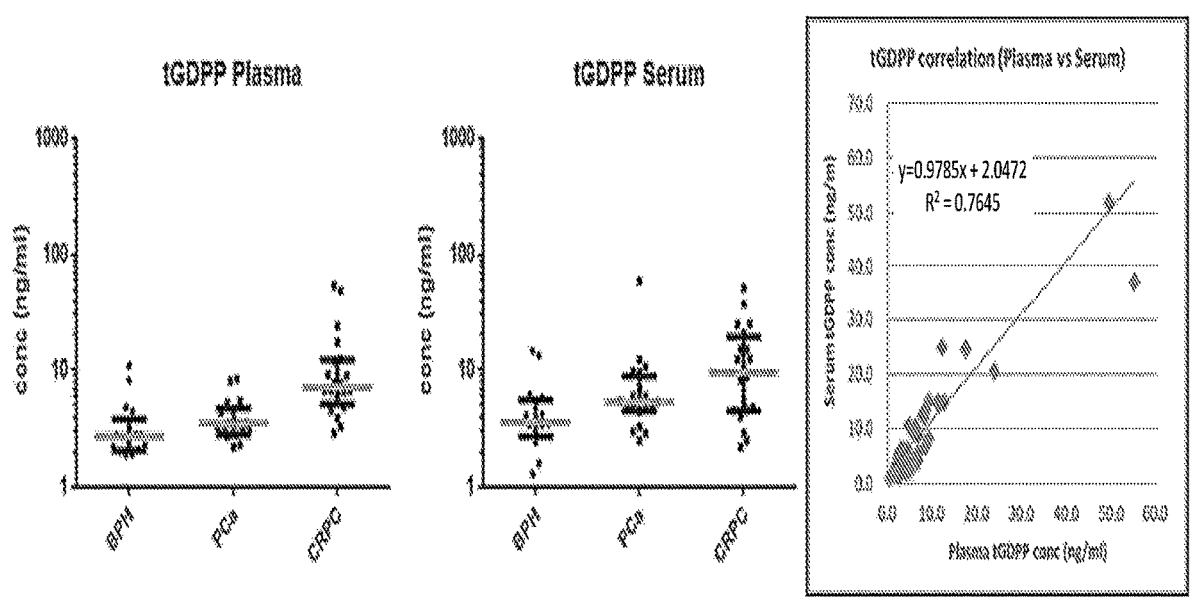
FIG. 7B is a diagram illustrating the results of AIA analysis of serum and plasma tGDPP in each prostate disease panel, and their correlations. Each horizontal bar represents the median in each disease group.
Figure 7C:
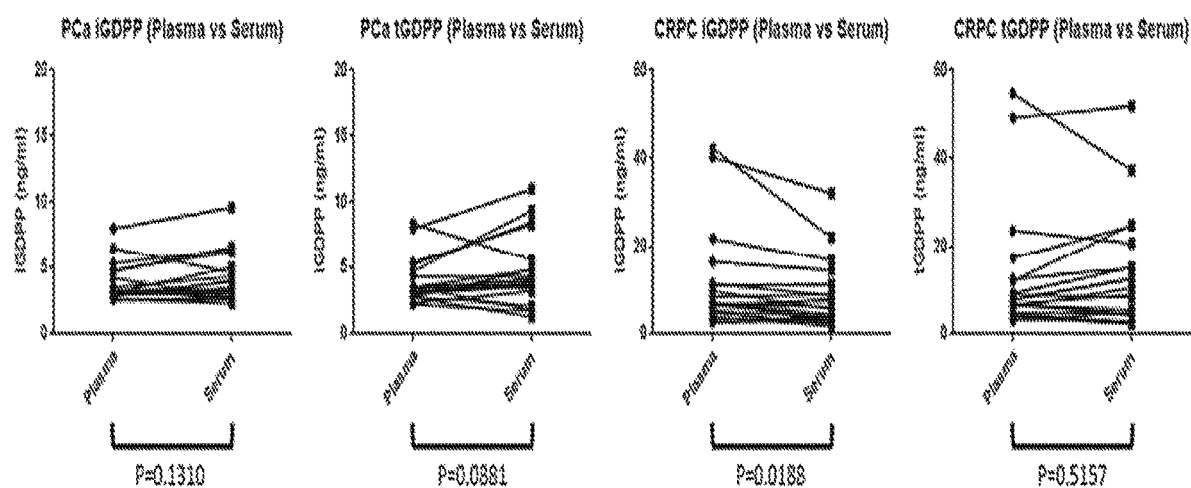
FIG. 7C is a diagram illustrating the serum-plasma differences in iGDPP and tGDPP measured values in the PCa and CRPC groups.

Table 4-1 and Table 4-2 show the results of measurement of iGDPP and tGDPP for samples whose serum and plasma were both available. As shown by the correlation diagrams of FIG. 7A and FIG. 7B, the concentration of iGDPP was smaller in serum than in plasma, and the concentration of tGDPP was almost the same between these. The serum-plasma differences in iGDPP and tGDPP in the PCa and CRPC groups are shown in FIG. 7C. In the PCa group, there was hardly a serum-plasma difference in either iGDPP or tGDPP. In contrast, in the CRPC group, while there was hardly a serum-plasma difference in tGDPP, the concentration of iGDPP in serum tended to be lower than in plasma. From these results, it was assumed that degradation of iGDPP occurs in serum, and that its effect is stronger in the CRPC group, wherein iGDPP is present at a higher concentration. Since the quantified values of iGDPP and tGDPP in plasma were almost the same, it was shown that the degradation hardly occurs in plasma. Since the plasma samples used herein were EDTA plasma, it is assumed that the protease involved in the degradation of GDPP is a protease whose deactivation occurs by a chelating agent.

TABLE 4-1

| | Plasma | | | | | |
|---|---|---|---|---|---|---|
| | iGDPP | | | tGDPP | | |
| | BPH | PCa | CRPC | BPH | PCa | CRPC |
| Minimum value | 1.0 | 2.5 | 2.6 | 0.5 | 2.2 | 2.9 |
| 25 Percentile | 2.3 | 2.9 | 5.5 | 2.1 | 2.8 | 5.1 |
| Median | 2.5 | 3.2 | 6.8 | 2.7 | 3.5 | 7.2 |
| 75 Percentile | 3.4 | 4.7 | 11.3 | 3.8 | 4.7 | 12.3 |
| Maximum value | 10.6 | 8.0 | 42.3 | 11.0 | 8.4 | 54.8 |
| 95% Confidence interval | 2.14 to 4.42 | 3.10 to 4.52 | 6.13 to 16.59 | 2.09 to 4.73 | 3.11 to 4.79 | 6.02 to 19.44 |

TABLE 4-2

| | Serum | | | | | |
|---|---|---|---|---|---|---|
| | iGDPP | | | tGDPP | | |
| | BPH | PCa | CRPC | BPH | PCa | CRPC |
| Minimum value | 1.4 | 2.3 | 1.7 | 1.4 | 4.1 | 3.7 |
| 25 Percentile | 2.2 | 2.7 | 3.6 | 4.45 | 7.375 | 7.45 |
| Median | 2.7 | 3.7 | 6.2 | 6.1 | 8.85 | 15.9 |
| 75 Percentile | 3.5 | 5.5 | 10.6 | 9.25 | 14.68 | 32.05 |
| Maximum value | 9.4 | 9.6 | 32.0 | 24.5 | 99.2 | 86.5 |
| 95% Confidence interval | 2.31 to 4.32 | 3.39 to 5.12 | 5.06 to 12.18 | 4.65 to 11.13 | 4.72 to 23.88 | 12.60 to 32.74 |

Figure 7D:
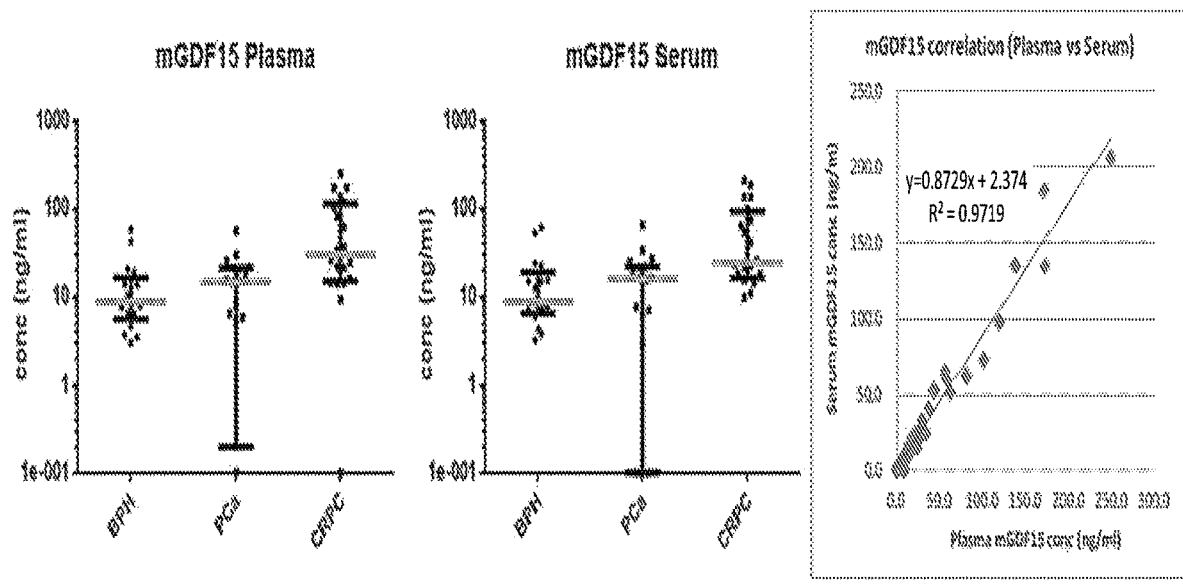
FIG. 7D is a diagram illustrating the results of AIA analysis of serum and plasma mGDF15 in each prostate disease panel, and their correlations. Each horizontal bar represents the median in each disease group.

As shown in Table 5 and FIG. 7D, almost the same result was obtained for mGDF15 in serum and plasma.

TABLE 5

| | mGDF15 | | | | | |
|---|---|---|---|---|---|---|
| | Plasma | | | Serum | | |
| | BPH | PCa | CRPC | BPH | PCa | CRPC |
| Minimum value | 3.0 | 6.6 | 0.1 | 3.2 | 0.6 | 0.0 |
| 25 Percentile | 5.6 | 0.2 | 15.0 | 6.5 | 0.1 | 16.2 |
| Median | 8.8 | 14.7 | 29.8 | 8.8 | 15.7 | 24.3 |
| 75 Percentile | 16.5 | 21.2 | 114.3 | 18.9 | 21.9 | 92.1 |
| Maximum value | 57.2 | 56.1 | 248.2 | 60.4 | 64.9 | 207.0 |

TABLE 5-continued

| | mGDF15 | | | | | |
|---|---|---|---|---|---|---|
| | Plasma | | | Serum | | |
| | BPH | PCa | CRPC | BPH | PCa | CRPC |
| 95% Confidence interval | 6.74 to 21.71 | 7.13 to 20.64 | 33.56 to 98.66 | 7.61 to 24.59 | 7.30 to 22.77 | 29.74 to 87.33 |

Figure 8A:
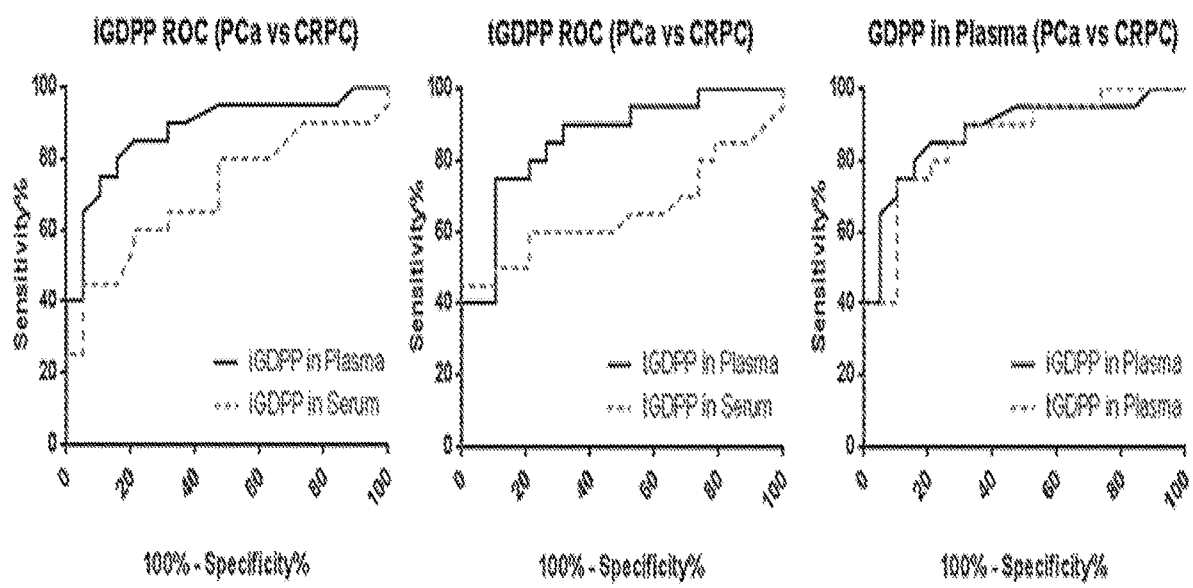
FIG. 8A is a diagram illustrating the ROC curves of iGDPP and tGDPP for PCa and CRPC samples. The solid lines represent values for plasma, and the broken lines represent values for serum.

Subsequently, the diagnostic performances of iGDPP and tGDPP were compared for cases of serum and plasma. As shown in Table 6-1, Table 6-2, and FIG. 8A, higher capacities to detect castration-resistant prostate cancer were shown when plasma was used for the measurement in both the cases of iGDPP and tGDPP. Since dNT-GDPP is hardly present in plasma, their diagnostic performances were almost the same. However, a slightly better diagnostic performance was shown in the case where iGDPP alone in plasma was measured. This is thought to be due to the fact that partial degradation occurs in high-expression samples.

Figure 8B:
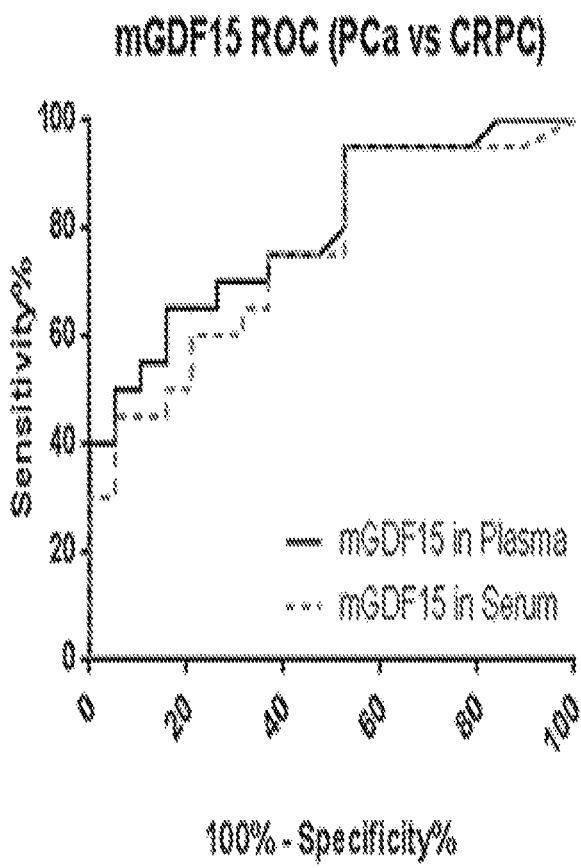
FIG. 8B is a diagram illustrating the ROC curves of mGDF15 for PCa and CRPC samples.

Regarding mGDF15, as shown in FIG. 8B, almost the same diagnostic performance was found between serum and plasma. Based on these results, it is thought that clinical evaluation of CRPC with GDPP is more preferably carried out by a method in which iGDPP in plasma is measured.

TABLE 6-1

| | iGDPP in Plasma | tGDPP in Plasma | mGDF15 in Plasma |
|---|---|---|---|
| Area under the curve | 0.8803 | 0.8605 | 0.7974 |
| Standard error | 0.0569 | 0.0598 | 0.07044 |
| 95% Confidence interval | 0.7687 to 0.9918 | 0.7434 to 0.9777 | 0.6593 to 0.9355 |
| P value | <0.0001 | 0.0001 | 0.0015 |

TABLE 6-2

| | iGDPP in Serum | tGDPP in Serum | mGDF15 in Serum |
|---|---|---|---|
| Area under the curve | 0.7000 | 0.6288 | 0.7579 |
| Standard error | 0.0851 | 0.0931 | 0.07709 |
| 95% Confidence interval | 0.5332 to 0.8668 | 0.4463 to 0.8112 | 0.6068 to 0.9090 |
| P value | 0.0305 | 0.1636 | 0.0059 |

In the following description, the AIA measurement results for the clinical samples are described only for those obtained with plasma, and the results for GDF15 propeptide are described only for those obtained for iGDPP.

Figure 9:
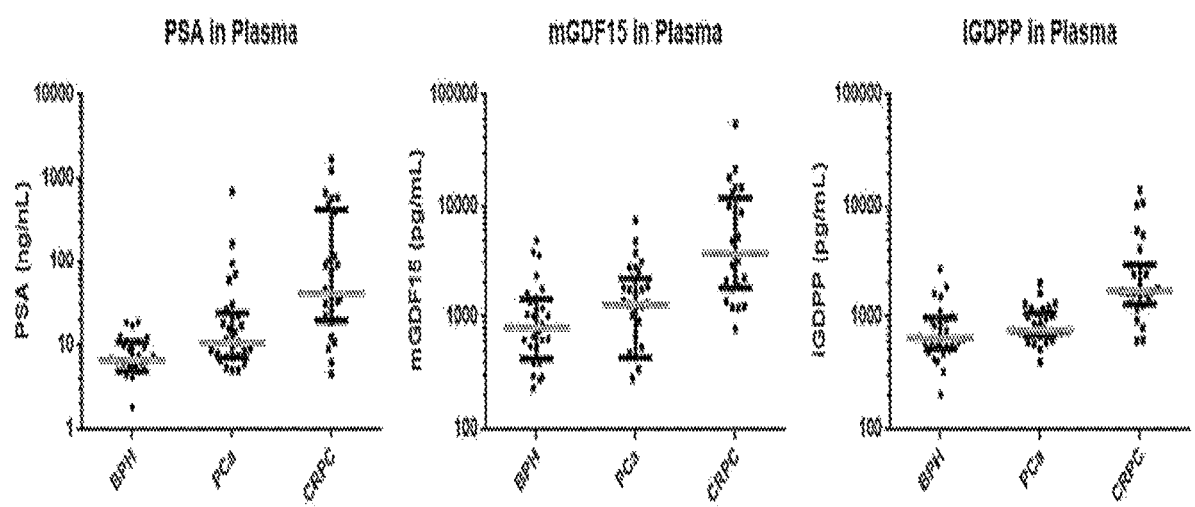
FIG. 9 is a diagram illustrating the results of AIA analysis of PSA, mGDF15, and iGDPP in prostate disease plasma.

The measured values of iGDPP and mGDF15, and the measured values of PSA are shown in FIG. 9. While mGDF15 and PSA tended to show high values generally in prostate cancer, GDPP characteristically showed high values in castration-resistant prostate cancer.

The results of analysis that was carried out after classification of the panel into three groups (benign prostatic hypertrophy, prostate cancer before acquisition of castration resistance, and castration-resistant prostate cancer) are shown in FIG. 9. The minimum value, the 25 percentile, the median, the 75 percentile, the maximum value, and the concentration range in the 95% confidence interval of the measured values of GDF15 propeptide, the measured values of the mature body of GDF15, and the measured values of PSA in each group are shown in Table 7, mGDF15 and PSA tended to show slightly higher values in prostate cancer before acquisition of castration resistance compared to benign prostatic hypertrophy, and showed remarkably high values in castration-resistant prostate cancer. However, since the concentration range overlapping between the cases before and after acquisition of castration resistance is wide, the diagnostic performance cannot be said to be high. On the other hand, GDPP hardly showed a difference between benign prostatic hypertrophy and prostate cancer before acquisition of castration resistance, and showed remarkably high values only in castration-resistant prostate cancer.

The difference between mGDF15 and GDPP is thought to be due to the difference in the secretion mechanism. It is assumed that, in prostate cancer before acquisition of castration resistance, mGDF15 alone is released from pro-GDF15 stored in the extracellular matrix, by the action of furin-like protease. In contrast, it is assumed that, in castration-resistant prostate cancer, an increased expression level causes release of not only mGDF15, but also GDPP that has become unable to be stored in the extracellular matrix into blood.

TABLE 7

| | | PSA | | | mGDF15 | | | iGDPP | | |
|---|---|---|---|---|---|---|---|---|---|---|
| | | BPH | PCa | CRPC | BPH | PCa | CRPC | BPH | PCa | CRPC |
| Minimum value | | 0.5 | 0.0 | 4.5 | 0.0 | 0.0 | 0.0 | 201.5 | 391.3 | 607.3 |
| 25 Percentile | | 4.9 | 7.1 | 19.2 | 421.1 | 432.6 | 1795.0 | 511.4 | 676.8 | 1288.0 |
| Median | | 6.6 | 10.6 | 40.5 | 798.1 | 1280.0 | 3720.0 | 643.5 | 765.0 | 1685.0 |
| 75 Percentile | | 10.7 | 23.8 | 427.1 | 1430.0 | 2182.0 | 11839.0 | 967.9 | 1080.0 | 2890.0 |
| Maximum value | | 18.5 | 695.5 | 1665.0 | 4912.0 | 7526.0 | 53937.0 | 2649.0 | 1997.0 | 14012.0 |
| 95% Confidence interval | | 6.09 to 9.72 | 2.33 to 96.09 | 78.89 to 414.7 | 734.2 to 1647 | 986.7 to 2177 | 3778 to 12408 | 619.7 to 1026 | 763.3 to 1020 | 1833 to 4510 |

Figure 10:
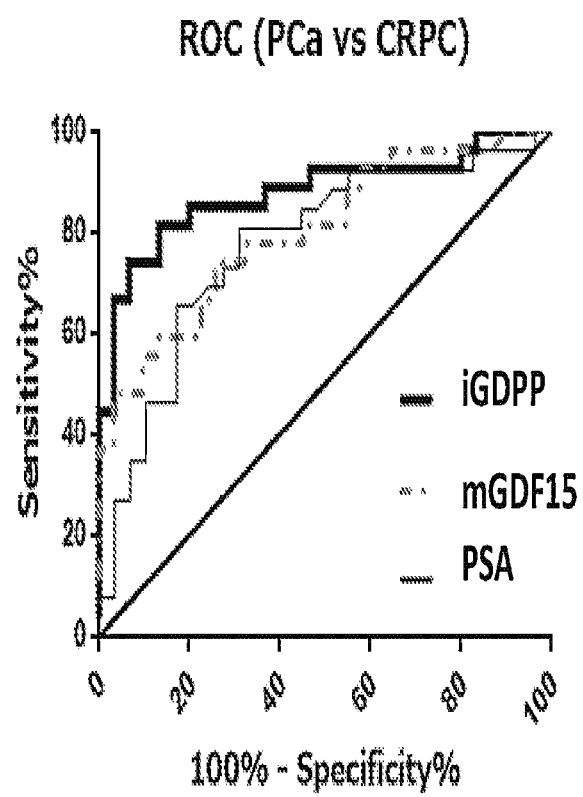
FIG. 10 is a diagram illustrating the ROC curves of PSA, mGDF15, and iGDPP for PCa and CRPC samples. The thin solid line represents PSA; the broken line represents mGDF15; and the thick solid line represents iGDPP.

The results of the receiver operating characteristic (ROC) curve analysis of the data obtained by the iGDPP assay system, mGDF15 assay system, and PSA measurement between the groups of prostate cancer before and after acquisition of castration resistance are shown in FIG. 10, and AUC (Area Under the Curve; area under the ROC curve) and the P-value in the significance test are shown in Table 8. The significant difference in the measured value of iGDPP between the groups of prostate cancer before and after acquisition of castration resistance was p<0.0001, which indicates a statistically significant difference, so that the iGDPP assay reagent was shown to be useful for detection of castration-resistant prostate cancer. It was also shown that the iGDPP assay system also shows a better P-value and a better AUC compared to the mGDF15 assay system and measured values of PSA.

TABLE 8

|  | PSA | mGDF15 | iGDPP |
|---|---|---|---|
| Area under the curve | 0.7732 | 0.8011 | 0.8790 |
| Standard error | 0.06498 | 0.05807 | 0.04877 |
| 95% Confidence interval | 0.6458 to 0.9006 | 0.6872 to 0.9149 | 0.7834 to 0.9746 |
| P value | 0.0005 | <0.0001 | <0.0001 |

Table 9 shows the sensitivity and the specificity between the groups of prostate cancer before and after acquisition of castration resistance as calculated by using the values obtained by the ROC analysis as reference values (cutoff values) for iGDPP and mGDF15 and using a value of 20 ng/mL, which is close to a common reference value, as a PSA reference value. Although the conditions were disadvantageous for PSA, usefulness of iGDPP became clear at least from the viewpoint of specific diagnosis of castration-resistant prostate cancer.

TABLE 9

|  | PSA | mGDF15 | iGDPP |
|---|---|---|---|
| Reference value | 20 | 1861 | 1337 |
| Sensitivity (%) | 73.1 | 74.1 | 74.1 |
| Specificity (%) | 69.0 | 74.2 | 93.3 |

Table 10 shows the positive rates for all clinical samples described in Example 10 as calculated by using the above reference values for iGDPP and mGDF15 and by using 20 ng/mL for PSA, which is a common reference value. In this panel, the iGDPP assay reagent showed a low false positivity, and allowed identification of castration-resistant prostate cancer based on positivity with a high probability. Thus, the reagent was shown to have a sufficient performance as a diagnostic marker for castration-resistant prostate cancer.

TABLE 10

|  |  | PSA | | mGDF15 | | iGDPP | |
|---|---|---|---|---|---|---|---|
|  | Number of cases | Number of positive cases | Positive rate (%) | Number of positive cases | Positive rate (%) | Number of positive cases | Positive rate (%) |
| Benign prostatic hypertrophy (BPH) | 28 | 0 | 0.0 | 4 | 14.3 | 4 | 14.3 |
| Prostate cancer (PCa) | 30 | 9 | 30.0 | 8 | 26.7 | 2 | 6.7 |
| Castration-resistant prostate cancer (CRPC) | 27 | 19 | 70.4 | 20 | 74.1 | 20 | 74.1 |
| Total | 85 |  |  |  |  |  |  |

The ability for identification of acquisition of castration resistance was compared among iGDPP, mGDF15, PSA, and the combination of iGDPP and PSA. As shown in Table 11, regarding the individual items, iGDPP showed the lowest values of both the false positivity and the false negativity, having the highest accuracy.

By the combination of iGDPP and PSA, the false negativity can be reduced. Future studies may enable further characterization of CRPC by comparison between high iGDPP cases and high PSA cases.

TABLE 11

|  | PSA | mGDF15 | iGDPP | PSA + iGDPP |
|---|---|---|---|---|
| Sensitivity (%) | 70.4 | 74.1 | 74.1 | 88.9 |
| Specificity (%) | 84.5 | 79.3 | 89.7 | 79.3 |
| False-positive rate (%) | 15.5 | 20.7 | 10.3 | 20.7 |
| False-negative rate (%) | 29.6 | 25.9 | 25.9 | 11.1 |
| Accuracy (%) | 67.9 | 62.5 | 76.9 | 66.7 |

Table 12 shows correlation coefficients between iGDPP and various parameters in each disease group.

Since iGDPP hardly showed correlation with the age and PSA, it was suggested to reflect a totally different event. On the other hand, although correlation between mGDF15 and iGDPP was found in CRPC, the correlation was characteristically low in PCa before acquisition of castration resistance. This is assumed to be due to a difference in the secretion mechanism which causes characteristic secretion of GDPP in CRPC.

EOD (Extent of Disease) and BSI (Bone Scan Index), which are indices of bone metastasis, do not show high correlations. Although mGDF15 has been reported to be a marker for bone metastasis, it tended to show high values also in PCa without bone metastasis. Thus, mGDF15 did not necessarily reflect the presence or absence of bone metastasis in the present result.

TABLE 12

| Correlation coefficient | | Age | PSA | mGDF15 | EOD | BSI |
|---|---|---|---|---|---|---|
| PCa iGDPP | Correlation | 0.0783 | 0.2490 | 0.2395 | No case of bone metastasis | |
| | P value | 0.5738 | 0.2014 | 0.2026 | | |
| CRPC iGDPP | Correlation | −0.1867 | 0.5673 | 0.8676 | 0.4935 | 0.3917 |
| | P value | 0.3714 | 0.0025 | <0.0001 | 0.0270 | 0.2335 |

<Example 11> Evaluation of CRPC Patient Plasma Samples During Follow-Up Period After Acquisition of Castration Resistance Table 13 shows iGDPP measurement results and PSA values of plasma samples, the conditions of administration of nonsteroidal anti-inflammatory drugs (NSAIDS), and the disease states, in 10 cases of CRPC patients during follow-up after acquisition of castration resistance.

All cases excluding CRPC-01 and CRPC-05 showed low values of both PSA and iGDPP, so that they were diagnosed to be under favorable control without progression of the cancer. However, when comparison is made between CRPC-05 (high PSA value/high iGDPP value) and CRPC-01 (high PSA value/low iGDPP value), both of which showed high PSA values, the former case showed malignant progression such as bone metastasis, but the latter case did not show malignant progression even with a high value of PSA, being diagnosed to be under favorable control. Based on the present result, it was suggested that iGDPP can be a marker that more accurately reflects malignant progression of CRPC than PSA.

Figure 11:
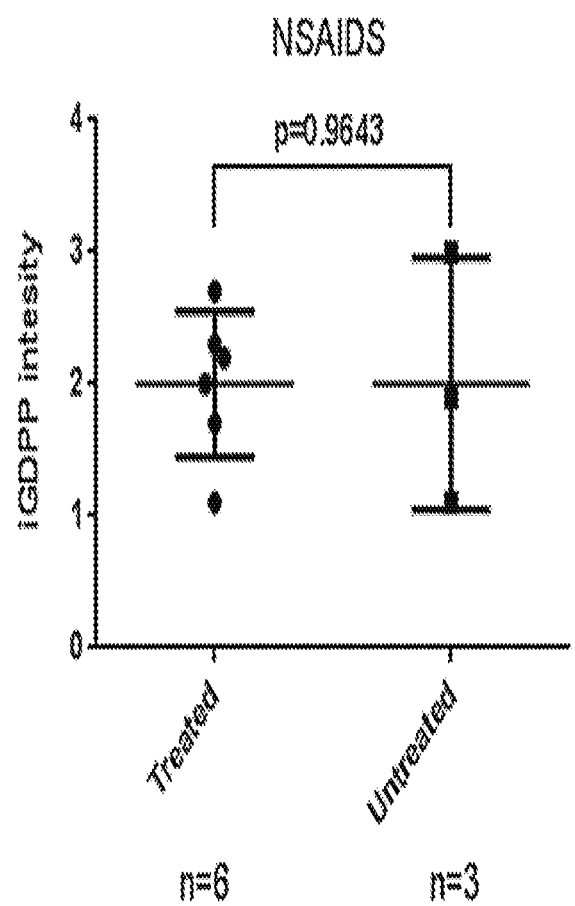
FIG. 11 is a diagram illustrating the measured values of iGDPP obtained with or without administration of a non-steroidal anti-inflammatory drug.

FIG. 11 shows the results of measurement of iGDPP in the NSAIDS administration group and the non-administration group, wherein all cases except CRPC-05, which showed malignant progression, were used. Since no significant difference was found between the groups by a Mann-Whitney test in the present study (p=0.9643), it was suggested that there may be no association between administration of NSAIDS and the blood iGDPP level.

TABLE 13

| Sample ID | PSA (ng/mL) | iGDPP (Signal intensity) | NSAIDS administration | Disease state |
|---|---|---|---|---|
| CRPC-01 | 481.0 | 2.0 | None | Good |
| CRPC-02 | 8.1 | 1.1 | None | Good |

TABLE 13-continued

| Sample ID | PSA (ng/mL) | iGDPP (Signal intensity) | NSAIDS administration | Disease state |
|---|---|---|---|---|
| CRPC-03 | 22.0 | 1.7 | None | Good |
| CRPC-04 | 0.2 | 1.1 | Calonal | Good |
| CRPC-05 | 622.3 | 60.2 | None | Poor (bone metastasis) |
| CRPC-06 | 3.9 | 2.3 | None | Good |
| CRPC-07 | 30.3 | 2.2 | None | Good |
| CRPC-08 | 0.1 | 2.7 | None | Good |
| CRPC-09 | 0.8 | 1.9 | Tramcet | Good |
| CRPC-10 | 36.7 | 3.0 | Loxonin | Good |

INDUSTRIAL APPLICABILITY

By the present invention, a method and a reagent for detecting GDF15 propeptide, which can be a novel detection marker for castration-resistant prostate cancer, are provided. These enable simple and highly accurate detection, by hemodiagnosis or the like, of acquisition of castration resistance, whose identification has been difficult by measurement of a conventional detection marker PSA alone. They are industrially very useful since they can simplify diagnosis of castration-resistant prostate cancer, thereby enabling selection of a therapeutic method in an early phase.

In prostate cancer in which changing of the therapeutic agent is necessary during the course of progression of the cancer, if identification of acquisition of castration resistance is possible with simple means such as hemodiagnosis, it may contribute to screening for castration-resistant prostate cancer and specification of the timing of changing the therapeutic agent at which the highest therapeutic effect can be expected. Further, future contribution to companion diagnosis for prostate cancer chemotherapies including use of novel therapeutic agents can be expected.

The invention claimed is:

1. A method for detecting castration-resistant prostate cancer, which comprises measuring intact growth and differentiation factor 15 (GDF15) propeptide level in a sample from a patient with prostate cancer.

2. The method according to claim 1, wherein the measurement is carried out using antigen-antibody reaction using an antibody that binds GDF15 propeptide.

3. The method according to claim 1, wherein the measurement is carried out using mass spectrometry.

4. A method for detecting castration-resistant prostate cancer, which comprises measuring growth and differentiation factor 15 (GDF15) propeptide fragment level in a sample from a patient with prostate cancer,
wherein the GDF15 propeptide fragment contains a GDF15 propeptide fragment(s) of the following (A) and/or (B):
(A) a GDF15 propeptide fragment having the following property (a):
(a) containing an amino acid sequence from the lysine of the 58th residue to at least the aspartic acid of the 167th residue in the GDF15 amino acid sequence of SEQ ID NO:2;
(B) a GDF15 propeptide fragment having the following property (c):
(c) containing an amino acid sequence from the glutamic acid of the 74th residue to at least the aspartic acid of the 167th residue in the GDF15 amino acid sequence of SEQ ID NO:2.

5. The method according to claim 4, wherein the GDF15 propeptide fragment (A) has the following property (b):
(b) separation into a fraction with a molecular weight of about 17,000 by reducing SDS-PAGE; and
the GDF15 propeptide fragment (B) has the following property (d):
(d) separation into a fraction with a molecular weight of about 15,000 by reducing SDS-PAGE.

6. The method according to claim 4, wherein the measurement is carried out using antigen-antibody reaction using an antibody that binds GDF15 propeptide.

7. The method according to claim 4, wherein the measurement is carried out using mass spectrometry.

8. A method for detecting castration-resistant prostate cancer, which comprises measuring the total of intact growth and differentiation factor 15 (GDF15) propeptide level and GDF15 propeptide fragment level in a sample from a patient with prostate cancer,
wherein the GDF15 propeptide fragment contains a GDF15 propeptide fragment(s) of the following (A) and/or (B):
(A) a GDF15 propeptide fragment having the following property (a):
(a) containing an amino acid sequence from the lysine of the 58th residue to at least the aspartic acid of the 167th residue in the GDF15 amino acid sequence of SEQ ID NO:2;
(B) a GDF15 propeptide fragment having the following property (c):
(c) containing an amino acid sequence from the glutamic acid of the 74th residue to at least the aspartic acid of the 167th residue in the GDF15 amino acid sequence of SEQ ID NO:2.

9. The method according to claim 8, wherein the GDF15 propeptide fragment (A) has the following property (b):
(b) separation into a fraction with a molecular weight of about 17,000 by reducing SDS-PAGE; and
the GDF15 propeptide fragment (B) has the following property (d):
(d) separation into a fraction with a molecular weight of about 15,000 by reducing SDS-PAGE.

10. The method according to claim 8, wherein the measurement is carried out using antigen-antibody reaction using an antibody that binds GDF15 propeptide.

11. The method according to claim 8, wherein the measurement is carried out using mass spectrometry.

* * * * *